US007166706B2

(12) United States Patent
Dumas et al.

(10) Patent No.: US 7,166,706 B2

(45) Date of Patent: Jan. 23, 2007

(54) USE OF KETOL-ACID REDUCTOISOMERASE INHIBITORS TO PREVENT OR TREAT FUNGAL INFECTION OF PLANTS

(75) Inventors: Renaud Dumas, Lyons (FR); Marc-Henri Lebrun, Lyons (FR); Jean-Luc Zundel, Lyons (FR); Géraldine Effantin, Saint Colombe (FR); Valérie Morin, Urou Et Grennoc (FR)

(73) Assignee: Bayer Cropscience S.A., Leclair (FR)

( * ) Notice: Subject to any disclaimer, the term of this patent is extended or adjusted under 35 U.S.C. 154(b) by 243 days.

(21) Appl. No.: 10/797,248

(22) Filed: Mar. 10, 2004

(65) Prior Publication Data

US 2004/0259848 A1 Dec. 23, 2004

Related U.S. Application Data

(63) Continuation of application No. PCT/FR02/03073, filed on Sep. 10, 2002.

(30) Foreign Application Priority Data

Sep. 10, 2001 (FR) .................................. 01 11689

(51) Int. Cl.

*C07K 16/00* (2006.01)
*C12N 5/06* (2006.01)
*C12N 5/16* (2006.01)

(52) U.S. Cl. ...................... 530/388.5; 514/12; 435/341

(58) Field of Classification Search ..................... None
See application file for complete search history.

(56) References Cited

U.S. PATENT DOCUMENTS 4,594,098 A 6/1986 Bauer et al.

FOREIGN PATENT DOCUMENTS

| | | |
|---|---|---|
| CA | 2002021 | 5/1990 |
| EP | 106114 | 4/1984 |
| EP | 196026 | 10/1986 |
| EP | 481407 | 4/1992 |
| WO | WO 94/23063 | 10/1994 |
| WO | WO 97/37660 | 10/1997 |

OTHER PUBLICATIONS

Dumas et al., Accounts of Chemical Research 34:399-408, 2001.
Halgand et al., Biochemistry 38:6025-6034, 1999.
Halgand et al., Biochemistry 37:4773-4781, 1998.
Wessel et al., Biochemistry 37:12753-12760, 1998.
Biou et al., EMBO J. 16:3405-3415, 1997.
Dumas et al., Febs Letters 408:156-160, 1997.
Dumas et al., Biochemistry 34:6026-6036, 1995.
Zelenaya-Troitskaya et al., EMBO J. 14:3268-3276, 1995.
Dumas et al., Biochem. J. 301:813-820, 1994.
Curien et al., Plant Mol. Biol. 21:717-722, 1993.
Dumas et al., Biochem. J. 294:821-828, 1993.
Dumas et al., Biochem. J. 288:865-874, 1992.
Sista et al., Gene, 120:115-118, 1992.
Dumas et al., Biochem. J. 277:469-475, 1991.
Wittenbach et al., Plant Physiol. 96, No. 1, Suppl., 94, 1991.
Schulz et al., FEBS Lett., 238:375-378, 1988.
Petersen, G.L. et al., NAR 14, 24:9631-9650, 1986.
Kritani et al., J. Biological Chemistry, 241:2047-2051, 1965.

*Primary Examiner*—B. Dell Chism
(74) *Attorney, Agent, or Firm*—Baker Botts L.L.P.

(57) ABSTRACT

The invention concerns the use of ketol-acid reductoisomerase inhibitors for treating fungal diseases affecting crops. The invention concerns methods for treating crops against fungal diseases comprising applying a ketol-acid reductoisomerase inhibitor. The invention also concerns methods for identifying novel fungicidal compounds comprising a step which consists in identifying ketol-acid reductoisomerase inhibitors.

8 Claims, 9 Drawing Sheets

```
M. grisea      MSARGFSKALRPMARQLATPAVQRRSFVAASSMVRATR--KAAVAPTQQQ
N. crassa      MAARNCTKALRPLARQLATPAVQRRTFVAAASAVRASVAVKAVAAPARQQ
S. cerevisae   ---MLRTQAARLICNSRVITAK--RTFALATRAAAYSRP-AARFVKPMIT
                     ..* * ..      *   *.*  *.  .  .    *

M. grisea      IRGVKTMDFAGHKEQVWERADWPKEKLLEYFKDDTLALIGYGSQGHGQGL
N. crassa      VRGVKTMDFAGHKEEVHERADWPAEKLLDYFKNDTLALIGYGSQGHGQGL
S. cerevisae   TRGLKQINFGGTVETVYERADWPREKLLDYFKNDTFALIGYGSQGYGQGL
                **.* . * *  * * ****** ****.*** ** ********* ****

M. grisea      NLRDNGLNVIIGVRKDGKSWKDAVQDGWVPGKNLFEVDEAISRGTVIMNL
N. crassa      NLRDNGLNVIVGVRKNGKSWEDAIQDGWVPGKNLFDVDEAISRGTIVMNL
S. cerevisae   NLRDNGLNVIIGVRKDGASWKAAIEDGWVPGKNLFTVEDAIKRGSYVMNL
               **********.**** * **  *..********** *..** **. .***

M. grisea      LSDAAQSETWPALKPQITKGKTLYFSHGFSPVFKDLTKVEVPTDVDVILC
N. crassa      LSDAAQSETWPHIKPQITKGKTLYFSHGFSPVFKDLTKVEVPTDVDVILV
S. cerevisae   LSDAAQSETWPAIKPLLTKGKTLYFSHGFSPVFKDLTHVEPPKDLDVILV
               *********** .** .********************.** * *.****

M. grisea      APKGSGRTVRSLFREGRGINSSFAVYQDVTGEAEEKAIALGVAIGSGYLY
N. crassa      APKGSGRTVRSLFREGRGINSSFAVYQDVTGKAKEKAVALGVAVGSGYLY
S. cerevisae   APKGSGRTVRSLFKEGRGINSSYAVWNDVTGKAHEKAQALAVAIGSGYVY
               *************.********.** .**** * *** ** **.****.*

M. grisea      KTTFEKEVYSDLYGERGCLMGGIHGMFLAQYEVLRERGHSPSEAFNETVE
N. crassa      ETTFEKEVYSDLYGERGCLMGGIHGMFLAQYEVLRERGHSPSEAFNETVE
S. cerevisae   QTTFEREVNSDLYGERGCLMGGIHGMFLAQYDVLRENGHSPSEAFNETVE
                ****.** **********************.**** *************

M. grisea      EATQSLYPLIGANGMDWMYEACSTTARRGAIDWSPRFKDALKPVFNQLYD
N. crassa      EATQSLYPLIGAHGMDWMFDACSTTARRGAIDWTPKFKDALKPVFNNLYD
S. cerevisae   EATQSLYPLIGKYGMDYMYDACSTTARRGALDWYPIFKNALKPVFQDLYE
               ***********  *** *..**********.** * ** ******. **.

M. grisea      SVKDGSETQRSLDYNSQPDYREKYEAEMEEIRNLEIWRAGKAVRSLRPEN
N. crassa      SVKNGDERKRSLEYNSQPDYRERYEAELDEIRNLEIWRAGK--RSLRPEN
S. cerevisae   STKNGTETKRSLEFNSQPDYREKLEKELDTIRNMEIWKVGKEVRKLRPEN
               * * * * .***..********. * *.. ***.***. **  * *****

M. grisea      QKQK
N. crassa      QK--
S. cerevisae   Q---
               *
```

Fig. 1

A
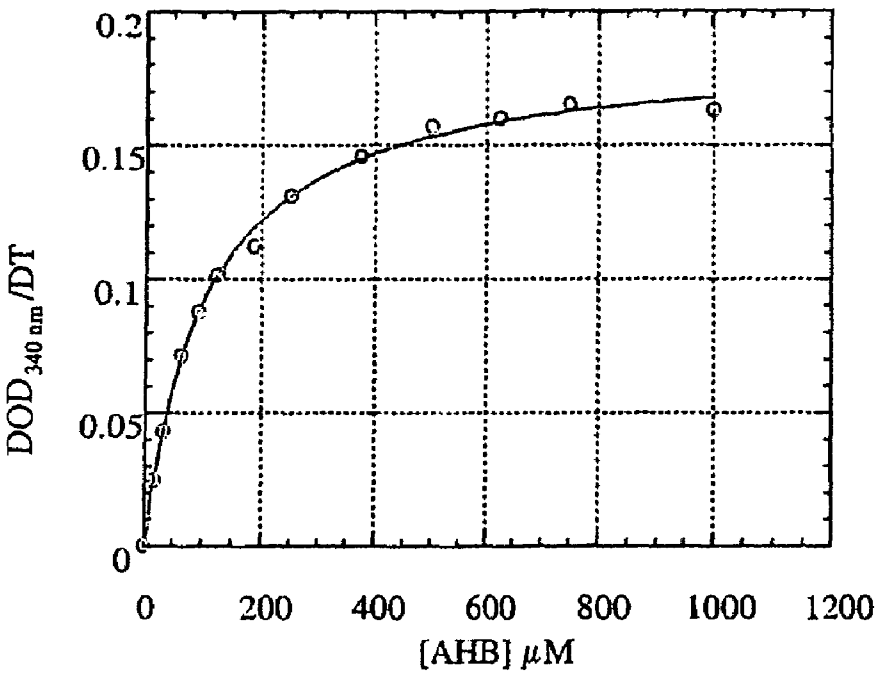
B
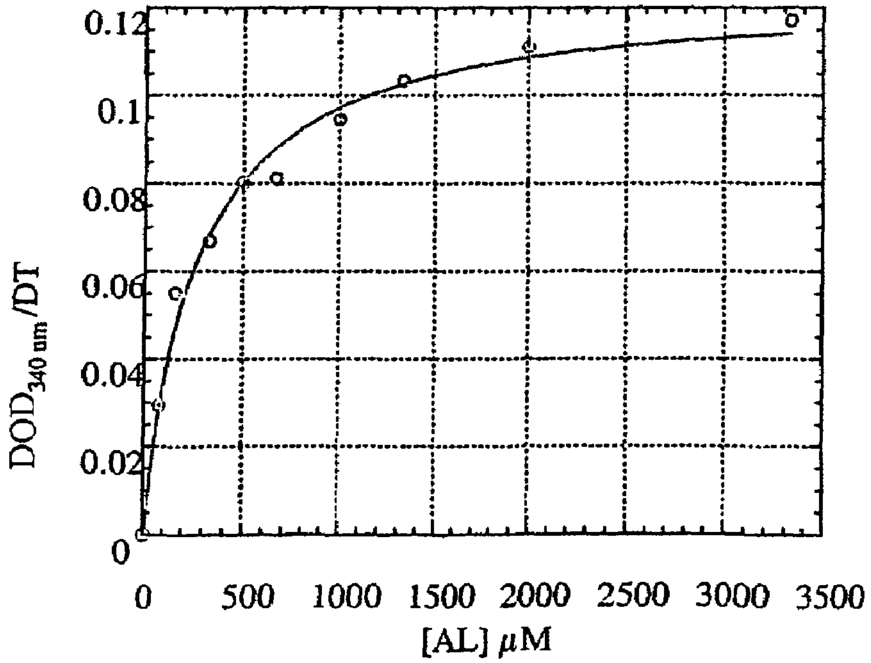
Fig.4 o control

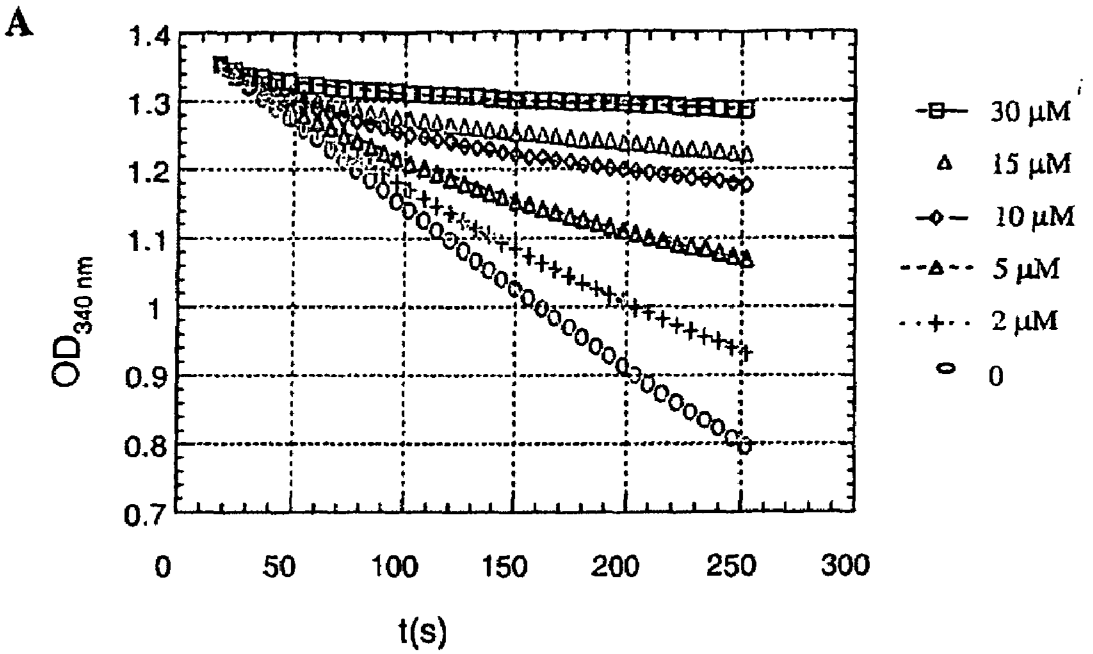
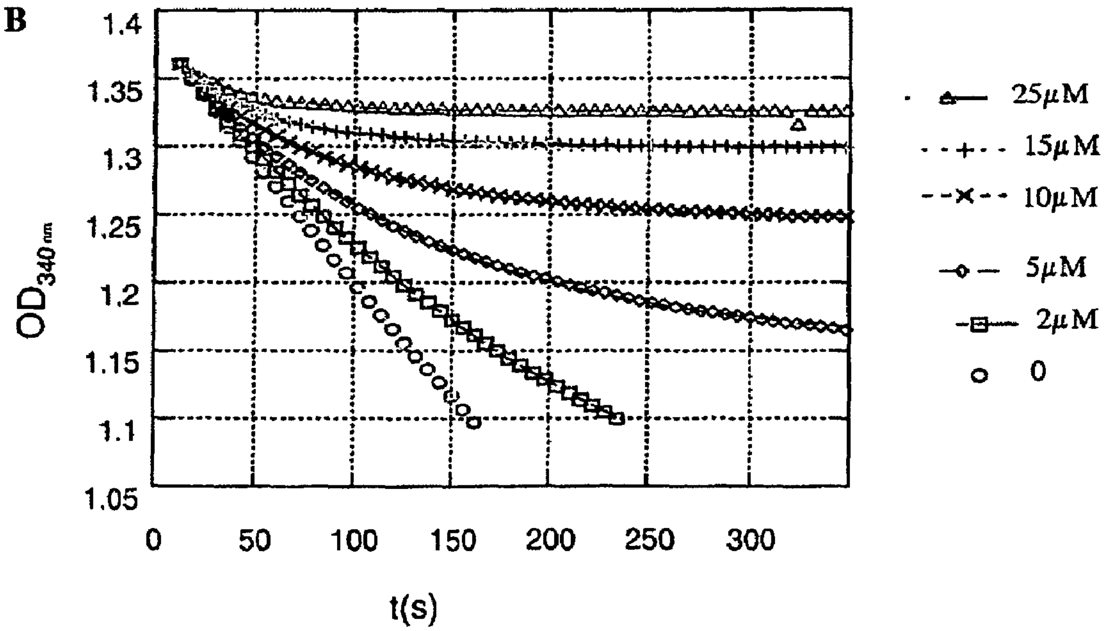
Fig.7

A
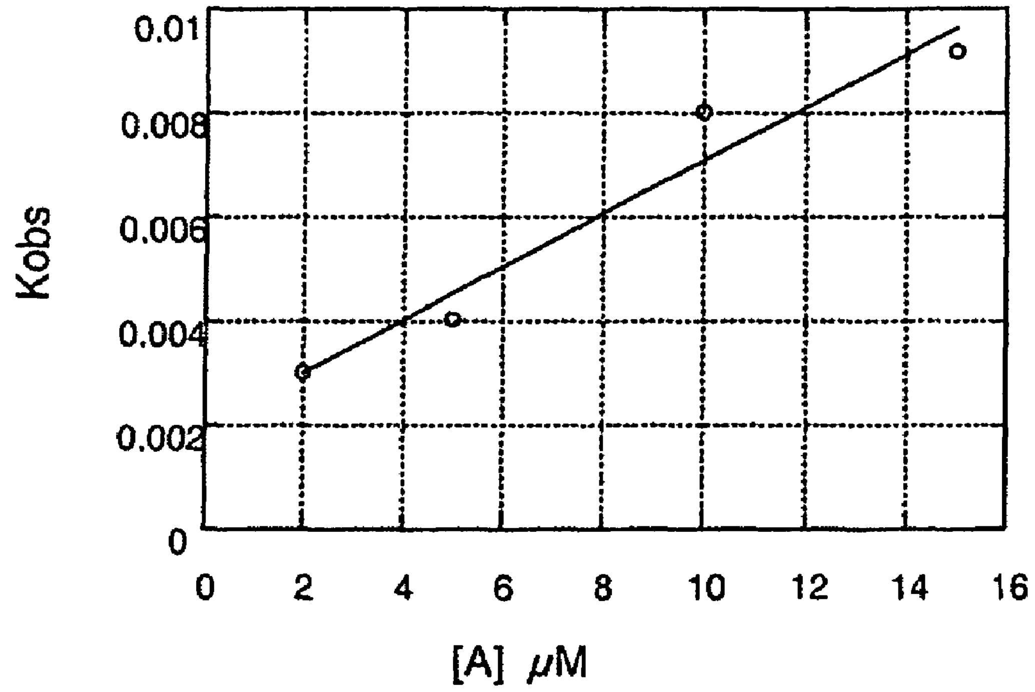
B
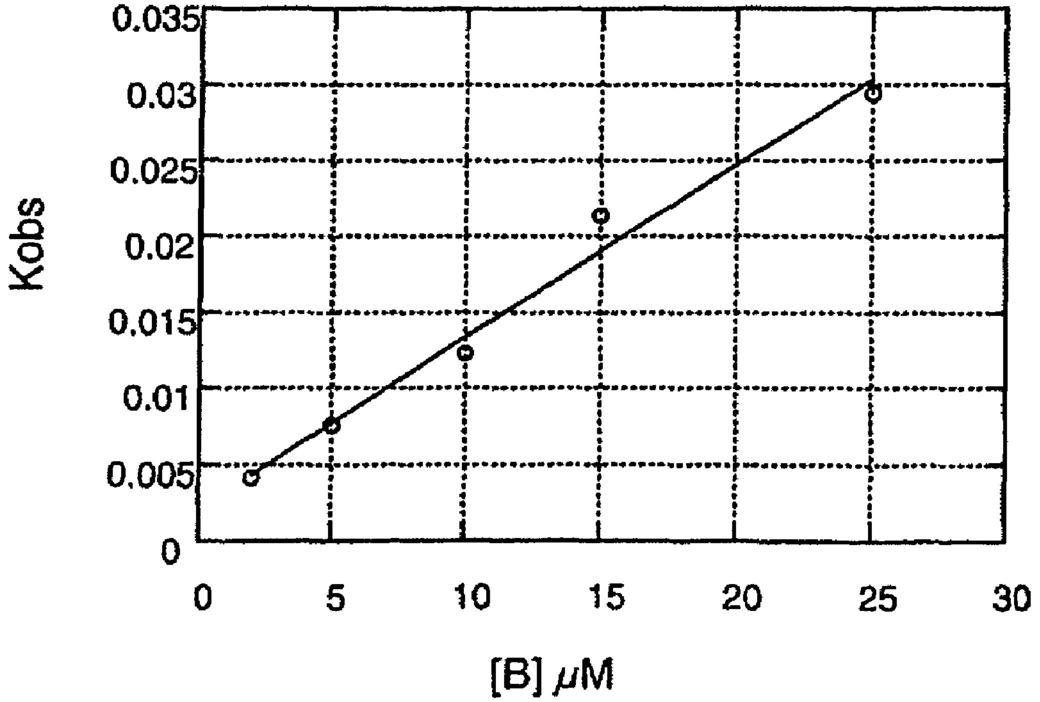
Fig. 8

A

B

SEQUENCE LISTING

```
<160> NUMBER OF SEQ ID NOS: 18

<210> SEQ ID NO 1
<211> LENGTH: 402
<212> TYPE: PRT
<213> ORGANISM: Magnaporthe grisea
<220> FEATURE:
<221> NAME/KEY: TRANSIT
<222> LOCATION: (1)..(51)
<223> OTHER INFORMATION: Putative mitochondrial transit peptide

<400> SEQUENCE: 1

Met Ser Ala Arg Gly Phe Ser Lys Ala Leu Arg Pro Met Ala Arg Gln
  1               5                  10                  15

Leu Ala Thr Pro Ala Val Gln Arg Arg Ser Phe Val Ala Ala Ser Ser
             20                  25                  30

Met Val Arg Ala Thr Arg Lys Ala Ala Val Ala Pro Thr Gln Gln Gln
         35                  40                  45

Ile Arg Gly Val Lys Thr Met Asp Phe Ala Gly His Lys Glu Gln Val
     50                  55                  60

Trp Glu Arg Ala Asp Trp Pro Lys Glu Lys Leu Leu Glu Tyr Phe Lys
 65                  70                  75                  80

Asp Asp Thr Leu Ala Leu Ile Gly Tyr Gly Ser Gln Gly His Gly Gln
                 85                  90                  95

Gly Leu Asn Leu Arg Asp Asn Gly Leu Asn Val Ile Ile Gly Val Arg
            100                 105                 110

Lys Asp Gly Lys Ser Trp Lys Asp Ala Val Gln Asp Gly Trp Val Pro
        115                 120                 125

Gly Lys Asn Leu Phe Glu Val Asp Glu Ala Ile Ser Arg Gly Thr Val
    130                 135                 140

Ile Met Asn Leu Leu Ser Asp Ala Ala Gln Ser Glu Thr Trp Pro Ala
145                 150                 155                 160

Leu Lys Pro Gln Ile Thr Lys Gly Lys Thr Leu Tyr Phe Ser His Gly
                165                 170                 175

Phe Ser Pro Val Phe Lys Asp Leu Thr Lys Val Glu Val Pro Thr Asp
            180                 185                 190

Val Asp Val Ile Leu Cys Ala Pro Lys Gly Ser Gly Arg Thr Val Arg
        195                 200                 205

Ser Leu Phe Arg Glu Gly Arg Gly Ile Asn Ser Ser Phe Ala Val Tyr
    210                 215                 220

Gln Asp Val Thr Gly Glu Ala Glu Glu Lys Ala Ile Ala Leu Gly Val
225                 230                 235                 240

Ala Ile Gly Ser Gly Tyr Leu Tyr Lys Thr Thr Phe Glu Lys Glu Val
                245                 250                 255

Tyr Ser Asp Leu Tyr Gly Glu Arg Gly Cys Leu Met Gly Gly Ile His
            260                 265                 270

Gly Met Phe Leu Ala Gln Tyr Glu Val Leu Arg Glu Arg Gly His Ser
        275                 280                 285

Pro Ser Glu Ala Phe Asn Glu Thr Val Glu Glu Ala Thr Gln Ser Leu
    290                 295                 300

Tyr Pro Leu Ile Gly Ala Asn Gly Met Asp Trp Met Tyr Glu Ala Cys
305                 310                 315                 320

Ser Thr Thr Ala Arg Arg Gly Ala Ile Asp Trp Ser Pro Arg Phe Lys
                325                 330                 335
```

-continued

```
Asp Ala Leu Lys Pro Val Phe Asn Gln Leu Tyr Asp Ser Val Lys Asp
            340                 345                 350

Gly Ser Glu Thr Gln Arg Ser Leu Asp Tyr Asn Ser Gln Pro Asp Tyr
        355                 360                 365

Arg Glu Lys Tyr Glu Ala Glu Met Glu Glu Ile Arg Asn Leu Glu Ile
    370                 375                 380

Trp Arg Ala Gly Lys Ala Val Arg Ser Leu Arg Pro Glu Asn Gln Lys
385                 390                 395                 400

Gln Lys


<210> SEQ ID NO 2
<211> LENGTH: 395
<212> TYPE: PRT
<213> ORGANISM: Saccharomyces cerevisiae
<220> FEATURE:
<221> NAME/KEY: TRANSIT
<222> LOCATION: (1)..(47)
<223> OTHER INFORMATION: mitochondrial transit peptide
<300> PUBLICATION INFORMATION:
<308> DATABASE ACCESSION NUMBER: gb:X04969
<309> DATABASE ENTRY DATE: 1993-09-12

<400> SEQUENCE: 2

Met Leu Arg Thr Gln Ala Ala Arg Leu Ile Cys Asn Ser Arg Val Ile
  1               5                  10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
 65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270
```

-continued

```
Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395


<210> SEQ ID NO 3
<211> LENGTH: 400
<212> TYPE: PRT
<213> ORGANISM: Neurospora crassa
<220> FEATURE:
<221> NAME/KEY: TRANSIT
<222> LOCATION: (1)..(53)
<223> OTHER INFORMATION: putative mitochondrial transit peptide
<300> PUBLICATION INFORMATION:
<308> DATABASE ACCESSION NUMBER: gb:M84189.1
<309> DATABASE ENTRY DATE: 1996-05-23

<400> SEQUENCE: 3

Met Ala Ala Arg Asn Cys Thr Lys Ala Leu Arg Pro Leu Ala Arg Gln
  1               5                  10                  15

Leu Ala Thr Pro Ala Val Gln Arg Arg Thr Phe Val Ala Ala Ala Ser
             20                  25                  30

Ala Val Arg Ala Ser Val Ala Val Lys Ala Val Ala Ala Pro Ala Arg
         35                  40                  45

Gln Gln Val Arg Gly Val Lys Thr Met Asp Phe Ala Gly His Lys Glu
     50                  55                  60

Glu Val His Glu Arg Ala Asp Trp Pro Ala Glu Lys Leu Leu Asp Tyr
 65                  70                  75                  80

Phe Lys Asn Asp Thr Leu Ala Leu Ile Gly Tyr Gly Ser Gln Gly His
                 85                  90                  95

Gly Gln Gly Leu Asn Leu Arg Asp Asn Gly Leu Asn Val Ile Val Gly
            100                 105                 110

Val Arg Lys Asn Gly Lys Ser Trp Glu Asp Ala Ile Gln Asp Gly Trp
        115                 120                 125

Val Pro Gly Lys Asn Leu Phe Asp Val Asp Glu Ala Ile Ser Arg Gly
    130                 135                 140

Thr Ile Val Met Asn Leu Leu Ser Asp Ala Ala Gln Ser Glu Thr Trp
145                 150                 155                 160

Pro His Ile Lys Pro Gln Ile Thr Lys Gly Lys Thr Leu Tyr Phe Ser
                165                 170                 175

His Gly Phe Ser Pro Val Phe Lys Asp Leu Thr Lys Val Glu Val Pro
            180                 185                 190

Thr Asp Val Asp Val Ile Leu Val Ala Pro Lys Gly Ser Gly Arg Thr
        195                 200                 205
```

-continued

```
Val Arg Ser Leu Phe Arg Glu Gly Arg Gly Ile Asn Ser Ser Phe Ala
    210                 215                 220

Val Tyr Gln Asp Val Thr Gly Lys Ala Lys Glu Lys Ala Val Ala Leu
225                 230                 235                 240

Gly Val Ala Val Gly Ser Gly Tyr Leu Tyr Glu Thr Thr Phe Glu Lys
                245                 250                 255

Glu Val Tyr Ser Asp Leu Tyr Gly Glu Arg Gly Cys Leu Met Gly Gly
            260                 265                 270

Ile His Gly Met Phe Leu Ala Gln Tyr Glu Val Leu Arg Glu Arg Gly
        275                 280                 285

His Ser Pro Ser Glu Ala Phe Asn Glu Thr Val Glu Glu Ala Thr Gln
    290                 295                 300

Ser Leu Tyr Pro Leu Ile Gly Ala His Gly Met Asp Trp Met Phe Asp
305                 310                 315                 320

Ala Cys Ser Thr Thr Ala Arg Arg Gly Ala Ile Asp Trp Thr Pro Lys
                325                 330                 335

Phe Lys Asp Ala Leu Lys Pro Val Phe Asn Asn Leu Tyr Asp Ser Val
            340                 345                 350

Lys Asn Gly Asp Glu Arg Lys Arg Ser Leu Glu Tyr Asn Ser Gln Pro
        355                 360                 365

Asp Tyr Arg Glu Arg Tyr Glu Ala Glu Leu Asp Glu Ile Arg Asn Leu
    370                 375                 380

Glu Ile Trp Arg Ala Gly Lys Arg Ser Leu Arg Pro Glu Asn Gln Lys
385                 390                 395                 400


<210> SEQ ID NO 4
<211> LENGTH: 1356
<212> TYPE: DNA
<213> ORGANISM: Magnaporthe grisea
<220> FEATURE:
<221> NAME/KEY: 5'UTR
<222> LOCATION: (1)..(43)
<220> FEATURE:
<221> NAME/KEY: CDS
<222> LOCATION: (44)..(1246)
<220> FEATURE:
<221> NAME/KEY: 3'UTR
<222> LOCATION: (1247)..(1356)
<220> FEATURE:
<221> NAME/KEY: polyA_site
<222> LOCATION: (1322)..(1330)

<400> SEQUENCE: 4

ttgtttttct tggttcctta ttctaccttg tcacacaaca aac atg tct gct cgc       55
                                                Met Ser Ala Arg
                                                  1

ggt ttc tca aag gct ttg agg cca atg gcc cgc caa ttg gcc act ccc      103
Gly Phe Ser Lys Ala Leu Arg Pro Met Ala Arg Gln Leu Ala Thr Pro
  5                  10                  15                  20

gcc gtt cag agg cgt acc ttc gtg gct gct tct agc atg gtg cgg gcc      151
Ala Val Gln Arg Arg Thr Phe Val Ala Ala Ser Ser Met Val Arg Ala
                 25                  30                  35

acc agg aaa gcc gcc gtc gct ccc act cag cag cag atc cgt ggt gtc      199
Thr Arg Lys Ala Ala Val Ala Pro Thr Gln Gln Gln Ile Arg Gly Val
             40                  45                  50

aag acc atg gat ttt gct ggc cac aag gag cag gtc tgg gag cgt gcc      247
Lys Thr Met Asp Phe Ala Gly His Lys Glu Gln Val Trp Glu Arg Ala
         55                  60                  65

gac tgg ccc aag gag aag ctg ctg gag tac ttc aag gac gac acc ctt      295
Asp Trp Pro Lys Glu Lys Leu Leu Glu Tyr Phe Lys Asp Asp Thr Leu
     70                  75                  80
```

-continued

```
gcc ctc atc ggc tat ggt tcg cag ggc cac ggc cag ggt ctt aac ctc      343
Ala Leu Ile Gly Tyr Gly Ser Gln Gly His Gly Gln Gly Leu Asn Leu
 85                  90                  95                 100

cgc gac aac ggc ctc aac gtc atc atc ggt gtg cgc aag gac gga aag      391
Arg Asp Asn Gly Leu Asn Val Ile Ile Gly Val Arg Lys Asp Gly Lys
                105                 110                 115

tcg tgg aag gac gcc gtc cag gac ggc tgg gtt ccc ggc aag aac ctc      439
Ser Trp Lys Asp Ala Val Gln Asp Gly Trp Val Pro Gly Lys Asn Leu
            120                 125                 130

ttc gag gtc gac gag gcc atc tcg cgc ggt acc gtc atc atg aac ctt      487
Phe Glu Val Asp Glu Ala Ile Ser Arg Gly Thr Val Ile Met Asn Leu
        135                 140                 145

ctg agc gac gct gcc cag agc gag acg tgg cct gct ctg aag ccc cag      535
Leu Ser Asp Ala Ala Gln Ser Glu Thr Trp Pro Ala Leu Lys Pro Gln
    150                 155                 160

atc act aag ggc aag act ctc tac ttc tcg cac ggt ttc tct ccc gtc      583
Ile Thr Lys Gly Lys Thr Leu Tyr Phe Ser His Gly Phe Ser Pro Val
165                 170                 175                 180

ttc aag gac ctc acc aag gtc gag gtc ccc acc gac gtc gac gtc atc      631
Phe Lys Asp Leu Thr Lys Val Glu Val Pro Thr Asp Val Asp Val Ile
                185                 190                 195

ctc tgc gcc ccc aag ggc tcc ggc cgc act gtc cgc tcg ctc ttc cgc      679
Leu Cys Ala Pro Lys Gly Ser Gly Arg Thr Val Arg Ser Leu Phe Arg
            200                 205                 210

gag ggt cgt ggc atc aac tcc tcc ttc gcc gtc tac cag gac gtg act      727
Glu Gly Arg Gly Ile Asn Ser Ser Phe Ala Val Tyr Gln Asp Val Thr
        215                 220                 225

ggc gag gct gaa gag aag gct atc gct ctc ggt gtt gcc att ggc agt      775
Gly Glu Ala Glu Glu Lys Ala Ile Ala Leu Gly Val Ala Ile Gly Ser
    230                 235                 240

ggt tac ctc tac aag acc acc ttc gag aag gag gtc tac tct gac ctg      823
Gly Tyr Leu Tyr Lys Thr Thr Phe Glu Lys Glu Val Tyr Ser Asp Leu
245                 250                 255                 260

tac ggt gag cgt ggc tgc ctg atg ggt ggt atc cac ggt atg ttc ctt      871
Tyr Gly Glu Arg Gly Cys Leu Met Gly Gly Ile His Gly Met Phe Leu
                265                 270                 275

gcc cag tac gag gtt ctc cgc gag cgt ggc cac agc ccc tcg gag gct      919
Ala Gln Tyr Glu Val Leu Arg Glu Arg Gly His Ser Pro Ser Glu Ala
            280                 285                 290

ttc aac gag act gtc gag gag gcc acc cag tct ctc tac ccc ctg atc      967
Phe Asn Glu Thr Val Glu Glu Ala Thr Gln Ser Leu Tyr Pro Leu Ile
        295                 300                 305

ggt gcc aac ggc atg gac tgg atg tac gag gcc tgc tct acc act gct     1015
Gly Ala Asn Gly Met Asp Trp Met Tyr Glu Ala Cys Ser Thr Thr Ala
    310                 315                 320

cgt cgt ggt gcc att gac tgg agc ccc cgc ttc aag gac gcc ctc aag     1063
Arg Arg Gly Ala Ile Asp Trp Ser Pro Arg Phe Lys Asp Ala Leu Lys
325                 330                 335                 340

ccc gtc ttc aac cag ctc tac gac tcg gtc aag gac ggc tct gag act     1111
Pro Val Phe Asn Gln Leu Tyr Asp Ser Val Lys Asp Gly Ser Glu Thr
                345                 350                 355

cag cgc tcg ctc gac tac aac agc cag ccc gac tac cgc gag aag tac     1159
Gln Arg Ser Leu Asp Tyr Asn Ser Gln Pro Asp Tyr Arg Glu Lys Tyr
            360                 365                 370

gag gcc gag atg gag gag atc cgc aac ctg gag atc tgg agg gcg ggt     1207
Glu Ala Glu Met Glu Glu Ile Arg Asn Leu Glu Ile Trp Arg Ala Gly
        375                 380                 385

aag gct gtg cgc agc ctc cgt cct gag aac cag aag taa actgtatatt      1256
Lys Ala Val Arg Ser Leu Arg Pro Glu Asn Gln Lys
```

-continued 390 395 400 tgcttccaag ttccggttaa atgccagtgg atctctacag agtgctggtg ggtggtcaat 1316 ttgttgaaaa ataatctgga gtcatcgcta catttcttgg 1356

<210> SEQ ID NO 5
<211> LENGTH: 400
<212> TYPE: PRT
<213> ORGANISM: Magnaporthe grisea

<400> SEQUENCE: 5

Met Ser Ala Arg Gly Phe Ser Lys Ala Leu Arg Pro Met Ala Arg Gln
1 5 10 15

Leu Ala Thr Pro Ala Val Gln Arg Arg Thr Phe Val Ala Ala Ser Ser
20 25 30

Met Val Arg Ala Thr Arg Lys Ala Ala Val Ala Pro Thr Gln Gln Gln
35 40 45

Ile Arg Gly Val Lys Thr Met Asp Phe Ala Gly His Lys Glu Gln Val
50 55 60

Trp Glu Arg Ala Asp Trp Pro Lys Glu Lys Leu Leu Glu Tyr Phe Lys
65 70 75 80

Asp Asp Thr Leu Ala Leu Ile Gly Tyr Gly Ser Gln Gly His Gly Gln
85 90 95

Gly Leu Asn Leu Arg Asp Asn Gly Leu Asn Val Ile Ile Gly Val Arg
100 105 110

Lys Asp Gly Lys Ser Trp Lys Asp Ala Val Gln Asp Gly Trp Val Pro
115 120 125

Gly Lys Asn Leu Phe Glu Val Asp Glu Ala Ile Ser Arg Gly Thr Val
130 135 140

Ile Met Asn Leu Leu Ser Asp Ala Ala Gln Ser Glu Thr Trp Pro Ala
145 150 155 160

Leu Lys Pro Gln Ile Thr Lys Gly Lys Thr Leu Tyr Phe Ser His Gly
165 170 175

Phe Ser Pro Val Phe Lys Asp Leu Thr Lys Val Glu Val Pro Thr Asp
180 185 190

Val Asp Val Ile Leu Cys Ala Pro Lys Gly Ser Gly Arg Thr Val Arg
195 200 205

Ser Leu Phe Arg Glu Gly Arg Gly Ile Asn Ser Ser Phe Ala Val Tyr
210 215 220

Gln Asp Val Thr Gly Glu Ala Glu Glu Lys Ala Ile Ala Leu Gly Val
225 230 235 240

Ala Ile Gly Ser Gly Tyr Leu Tyr Lys Thr Thr Phe Glu Lys Glu Val
245 250 255

Tyr Ser Asp Leu Tyr Gly Glu Arg Gly Cys Leu Met Gly Gly Ile His
260 265 270

Gly Met Phe Leu Ala Gln Tyr Glu Val Leu Arg Glu Arg Gly His Ser
275 280 285

Pro Ser Glu Ala Phe Asn Glu Thr Val Glu Glu Ala Thr Gln Ser Leu
290 295 300

Tyr Pro Leu Ile Gly Ala Asn Gly Met Asp Trp Met Tyr Glu Ala Cys
305 310 315 320

Ser Thr Thr Ala Arg Arg Gly Ala Ile Asp Trp Ser Pro Arg Phe Lys
325 330 335

Asp Ala Leu Lys Pro Val Phe Asn Gln Leu Tyr Asp Ser Val Lys Asp
340 345 350

-continued

Gly Ser Glu Thr Gln Arg Ser Leu Asp Tyr Asn Ser Gln Pro Asp Tyr
355 360 365

Arg Glu Lys Tyr Glu Ala Glu Met Glu Glu Ile Arg Asn Leu Glu Ile
370 375 380

Trp Arg Ala Gly Lys Ala Val Arg Ser Leu Arg Pro Glu Asn Gln Lys
385 390 395 400

<210> SEQ ID NO 6
<211> LENGTH: 3827
<212> TYPE: DNA
<213> ORGANISM: Magnaporthe grisea
<220> FEATURE:
<221> NAME/KEY: promoter
<222> LOCATION: (1)..(1460)
<220> FEATURE:
<221> NAME/KEY: 5'UTR
<222> LOCATION: (1461)..(1503)
<220> FEATURE:
<221> NAME/KEY: intron
<222> LOCATION: (1700)..(1781)
<220> FEATURE:
<221> NAME/KEY: intron
<222> LOCATION: (1814)..(1890)
<220> FEATURE:
<221> NAME/KEY: intron
<222> LOCATION: (2170)..(2255)
<220> FEATURE:
<221> NAME/KEY: 3'UTR
<222> LOCATION: (2952)..(3061)
<220> FEATURE:
<221> NAME/KEY: terminator
<222> LOCATION: (3062)..(3827)

<400> SEQUENCE: 6
ccgagtttcc cgaccccgac gacatcctca actttaggct tatcatcgag cccggcgagg 60
gcatgtaccg cggcgggcga ttcactttcg acttcaagat taaccaaaac ttcccgcatg 120
agccaccaaa ggtcttgtgt gaacagaaga tctaccatcc caatatcgat ctagagggca 180
aggtttgcct gaacattctg cgtgaggatt ggaagccggt cctgaacctc aacgccgtca 240
ttgttggtct tcaggtacgt ccaaatatag ctttgatgcc cgacctgtta catcctatat 300
gtgacacaac atactcaaaa gactcgtagc tctatacgtg agcagtggca caatgtaaaa 360
caactggaat cagaaaacgc taaccagacc acttcgtgtc gtcttagttc cttttcctcg 420
agcccaacgc ctcggacccg ctgaacaagg acgcggctga agacctcaga agcaaccggg 480
agggcttcaa acgtaacgtc cggacctcca tgggcggagg ggcagtcaag gggatttctt 540
tcgatcgcgt tctgaaataa agataggcgg aaggaaggca aactctgctg caaagagaac 600
atgataccct cctactaaga ctcaagagtc gcaacctgtg ccatgggaac gatcatttct 660
atcccgaccg cgaaacctac gcgtcggcgt cccagcggtg gctatgagtg agtcatctgg 720
atgcctggaa cattcaggac aatagacccc agggagtcat ctcagtgccc agaaggcaaa 780
catggttgaa tgcgagaata agccggggag gtgaatggat ggcgacgagg gttttctcgc 840
tggccattgg acttcctaga cctagttcta aatacggagt atcggaacat aagatgggtg 900
gggcaagcgg tgtcgatttt tagcgatttc ggcggtctgt attttcaaca ttggcggttt 960
ctgctttctt atttcaccct ctattaagat ctacctcatc tccccaataa atacataaat 1020
ctagatcgtt ttcatgtctt taagaacata gattgaggct ttttgtacgt gaatggctgg 1080
tttcaaaaga atgactcgat tggctgagta atgaatttta tctcgtggtt gttattatgg 1140
aattaggcga aagcctatcc ggtcgtcgtc gataacgctg acccaagagg cttctccggt 1200

-continued

```
ttggagagct gctggttctt ggtagatcaa agcggggcat ctgggtctgg ggctccgtta   1260

tgcgggcggt ctccaccgga gctaccctgc ttttcaaaac ggtccgatat cgctggccta   1320

ggaaaatttt gtacccacaa tgcctaagtc ggagctgctc cttagtgttg agttttgttg   1380

aagctcgctc ctaaattcat cttcattcga ctttccattg tcggtgaata cggattccct   1440

ttctctccat ctccactcaa ttgtttttct tggttcctta ttctaccttg tcacacaaca   1500

aacatgtctg ctcgcggttt ctcaaaggct ttgaggccaa tggcccgcca attggccact   1560

cccgccgttc agaggcgtac cttcgtggct gcttctagca tggtgcgggc caccaggaaa   1620

gccgccgtcg ctcccactca gcagcagatc cgtggtgtca agaccatgga ttttgctggc   1680

cacaaggagc aggtctgggg tgagttggac agctcaattg ctcaattcgc ggctcaatga   1740

attcgtaaac tgacaggctt tttttcggtc taccaatcta gagcgtgccg actggcccaa   1800

ggagaagctg ctggtgagtc atgtcatttt tttttgcctg acaattccac caacttcaag   1860

cagtcaaaat actaatcact tgaactacag gagtacttca aggacgacac ccttgccctc   1920

atcggctatg gttcgcaggg ccacggccag ggtcttaacc tccgcgacaa cggcctcaac   1980

gtcatcatcg gtgtgcgcaa ggacggaaag tcgtggaagg acgccgtcca ggacggctgg   2040

gttcccggca agaacctctt cgaggtcgac gaggccatct cgcgcggtac cgtcatcatg   2100

aaccttctga gcgacgctgc ccagagcgag acgtggcctg ctctgaagcc ccagatcact   2160

aagggcaagg tatgtggcgc ttaagactga ccgtttcttt ttacttaccc cgctgcttta   2220

taagaataaa aaagagctaa caagtcttta tgtagactct ctacttctcg cacggtttct   2280

ctcccgtctt caaggacctc accaaggtcg aggtccccac cgacgtcgac gtcatcctct   2340

gcgcccccaa gggctccggc cgcactgtcc gctcgctctt ccgcgagggt cgtggcatca   2400

actcctcctt cgccgtctac caggacgtga ctggcgaggc tgaagagaag gctatcgctc   2460

tcggtgttgc cattggcagt ggttacctct acaagaccac cttcgagaag gaggtctact   2520

ctgacctgta cggtgagcgt ggctgcctga tgggtggtat ccacggtatg ttccttgccc   2580

agtacgaggt tctccgcgag cgtggccaca gcccctcgga ggctttcaac gagactgtcg   2640

aggaggccac ccagtctctc tacccccctga tcggtgccaa cggcatggac tggatgtacg   2700

aggcctgctc taccactgct cgtcgtggtg ccattgactg gagcccccgc ttcaaggacg   2760

ccctcaagcc cgtcttcaac cagctctacg actcggtcaa ggacggctct gagactcagc   2820

gctcgctcga ctacaacagc cagcccgact accgcgagaa gtacgaggcc gagatggagg   2880

agatccgcaa cctggagatc tggagggcgg gtaaggctgt gcgcagcctc cgtcctgaga   2940

accagaagta aactgtatat ttgcttccaa gttccggtca aatgccagtg gatctctaca   3000

gagtgctggt gggtggtcaa tttgttgaaa aataatctgg agtcatcgct acatttcttg   3060

gaatatcgcg gggttctgtg tccaaaaagc ttgcggtatt tcgatcgggt ttgcttttaa   3120

tgtttatcag atttcatctt tgtctgggat tacatcagtc tactatacct cgccatttta   3180

aattggtatc ttttttttcgt ctttacctgc ttattcaact gtccccatgc tactgtgccg   3240

cttttgattc atcttctcca tggcgccttg gcagttgttt tgcgagttcc acaaaacctc   3300

cttcttggtc accaccaagg gtgatccaaa tgtcaaccca tcgccgggca tcctcgtagc   3360

gctcttcgga cctaatccat tcttcctcac ccacgcgctc aaggtatacg gtacgcaagc   3420

cgcaggcttt tgcgcccttg aggtcgccta agtgggcagc aaccatggca acctcatccg   3480

ggcgcaggcc caagccctca acagctccca agtacgtcct tgggtttggc ttgtatgcac   3540

caaagtcctc agccgagaag agacgatcga accccaggcc atcgtggtag gtgttgaggt   3600
```

-continued cctgcagcag agactggttg ccgttagaca aggcggccgt gaccagaccc cggctcgcca 3660
gccgcgcgag accttgacgg gtatcgggcc agggctccag cctatgccac gcccgactca 3720
actccagcac ctcatcgtcc gtgaacaggc cggctagtcc tcgctcctcg agcagacgct 3780
cgaggctctc gcggtggtgc gtgtcaatgt ccttccaggg cgtgatg 3827

<210> SEQ ID NO 7
<211> LENGTH: 20
<212> TYPE: DNA
<213> ORGANISM: Artificial sequence
<220> FEATURE:
<223> OTHER INFORMATION: Description of the artificial sequence: primer
1

<400> SEQUENCE: 7
gaytayttya araaygayac 20

<210> SEQ ID NO 8
<211> LENGTH: 20
<212> TYPE: DNA
<213> ORGANISM: Artificial sequence
<220> FEATURE:
<223> OTHER INFORMATION: Description of the artificial sequence: primer
2
<220> FEATURE:
<221> NAME/KEY: VARIANT
<222> LOCATION: (9)...(12)
<223> OTHER INFORMATION: n = a, c, g, or t

<400> SEQUENCE: 8
atgttyytng cncartayga 20

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence: primer
3
<220> FEATURE:
<221> NAME/KEY: VARIANT
<222> LOCATION: (6)...(18)
<223> OTHER INFORMATION: n = a, c, g, or t

<400> SEQUENCE: 9
gayggntggg tnccnggnaa 20

<210> SEQ ID NO 10
<211> LENGTH: 21
<212> TYPE: DNA
<213> ORGANISM: Artificial sequence
<220> FEATURE:
<223> OTHER INFORMATION: Description of the artificial sequence: primer
4
<220> FEATURE:
<221> NAME/KEY: VARIANT
<222> LOCATION: (6)...(18)
<223> OTHER INFORMATION: n = a, c, g, or t

<400> SEQUENCE: 10
atgggnggna tacayggnat g 21

<210> SEQ ID NO 11
<211> LENGTH: 29
<212> TYPE: DNA
<213> ORGANISM: Artificial sequence
<220> FEATURE:

-continued

<223> OTHER INFORMATION: Description of the artificial sequence: primer 2'

<400> SEQUENCE: 11
ctgcttccat ggcaccagct gcccgtttc 29

<210> SEQ ID NO 12
<211> LENGTH: 29
<212> TYPE: DNA
<213> ORGANISM: Artificial sequence
<220> FEATURE:
<223> OTHER INFORMATION: Description of the artificial sequence: primer 1'

<400> SEQUENCE: 12
ctacccccat ggtgaagcaa atcaacttc 29

<210> SEQ ID NO 13
<211> LENGTH: 36
<212> TYPE: DNA
<213> ORGANISM: Artificial sequence
<220> FEATURE:
<223> OTHER INFORMATION: Description of the artificial sequence: primer 3'

<400> SEQUENCE: 13
gcacttgata ttattgtcga ctttattggt tttctg 36

<210> SEQ ID NO 14
<211> LENGTH: 20
<212> TYPE: DNA
<213> ORGANISM: Artificial sequence
<220> FEATURE:
<223> OTHER INFORMATION: Description of the artificial sequence: primer 13U

<400> SEQUENCE: 14
aacgacaccc ttgccctcat 20

<210> SEQ ID NO 15
<211> LENGTH: 20
<212> TYPE: DNA
<213> ORGANISM: Artificial sequence
<220> FEATURE:
<223> OTHER INFORMATION: Description of the artificial sequence: primer 300U

<400> SEQUENCE: 15
accgtttctt tttacttacc 20

<210> SEQ ID NO 16
<211> LENGTH: 20
<212> TYPE: DNA
<213> ORGANISM: Artificial sequence
<220> FEATURE:
<223> OTHER INFORMATION: Description of the artificial sequence: primer 549L

<400> SEQUENCE: 16
gcgatagcct tctcttcagc 20

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence: primer -continued

```
      22U

<400> SEQUENCE: 17

ttgtttttct tggttcctta                                             20


<210> SEQ ID NO 18
<211> LENGTH: 20
<212> TYPE: DNA
<213> ORGANISM: Artificial sequence
<220> FEATURE:
<223> OTHER INFORMATION: Description of the artificial sequence: Primer
      1603L

<400> SEQUENCE: 18

ccaagaaatg tagcgatgac                                             20
```

USE OF KETOL-ACID REDUCTOISOMERASE INHIBITORS TO PREVENT OR TREAT FUNGAL INFECTION OF PLANTS

This application is a continuation of International Patent application No. PCT/FR02/03073 filed Sep. 10, 2002 and published in French as WO 03/022056 on Mar. 20, 2003, which claims priority to French Patent Application No. FR 01/11,689 filed Sep. 10, 2001.

FIELD OF THE INVENTION

The present invention relates to the use of ketol-acid reductoisomerase inhibitors for treating fungal diseases affecting crops.

BACKGROUND OF THE INVENTION

Fungi are responsible for devastating epidemics which can lead to considerable losses of crops of various plant species. The principle of employing inhibitors of enzymes from pathogenic fungi, and of using these enzymes in tests for identifying novel molecules which are active against these fungi is known per se. However, simple characterization of a fungal enzyme is not sufficient to achieve this aim, the enzyme chosen as a target for potential fungicidal molecules also has to be essential to the life of the fungus, its inhibition by the fungicidal molecule resulting in death of the fungus, or essential to the pathogenesis of the fungus, its inhibition not being lethal for the fungus, but simply inhibiting its pathogenic potency. The identification of metabolic pathways and of enzymes essential to the pathogenesis and to the survival of the fungus is therefore necessary for the development of novel fungicidal products.

Ketol-acid reductoisomerase is an enzyme which has been well characterized in plants and microorganisms such as bacteria and yeast. This enzyme is the second enzyme of the biosynthetic pathway for branched-chain amino acids; it catalyzes conversion of the substrate 2S-2-acetolactate (AL) or 2S-2-aceto-2-hydroxybutyrate (AHB) to 2,3-dihydroxy-3-isovalerate (DHIV) or to 2,3-dihydroxy-3-methylvalerate (DHIM), respectively. This reaction requires the presence of magnesium ions ($Mg^{2+}$) and occurs in two steps: isomerization of a methyl or ethyl group, followed by reduction by NADPH. A great deal of knowledge has been acquired regarding plant reductoisomerase as a target for herbicides (Wittenbach et al., *Plant Physiol.* 96, No. 1, Suppl., 94, 1991; Schulz et al., *FEBS Lett.,* 238:375–378, 1988) and ketol-acid reductoisomerase inhibitors have been described as herbicides (EP106114; U.S. Pat. No. 4,594,098, EP196026, EP481407, WO 94/23063, CA2002021). However, these compounds have not shown effective herbicidal activity on plants.

A subject of the present invention is methods for treating crops against fungal diseases, comprising applying a ketol-acid reductoisomerase inhibitor. It has been found that inactivation of the ILV5 gene encoding ketol-acid reductoisomerase in *Magnaporthe grisea* results in inhibition of fungal growth. This inhibition of fungal growth is also observed in vivo in the presence of inhibitors specific for ketol-acid reductoisomerase. *M. grisea* is pathogenic for many species of crop plants such as rice.

SUMMARY OF THE INVENTION

The invention relates to the use of ketol-acid reductoisomerase inhibitors for treating fungal diseases affecting crops. The invention provides antifungal compositions comprising a ketol-acid reductoisomerase inhibitor. The invention also provides methods for treating crops against fungal diseases comprising applying a ketol-acid reductoisomerase inhibitor, e.g. to seeds, roots, and/or shoots. The invention further provides methods for identifying novel fungicidal compounds comprising identifying ketol-acid reductoisomerase inhibitors.

DESCRIPTION OF THE FIGURES

FIG. 1: Comparison of the protein sequences of the reductoisomerases of *M. grisea* (SEQ ID NO:1) and *N. crassa* (SEQ ID NO:3) and of the yeast *S. cerevisiae* (SEQ ID NO:2). Sequence alignment using the CLUSTAL W(1.4)™ software. Symbols: ":" marks similar amino acids; "*" marks identical amino acids.

The effect of the inhibitor IpOHA is tested on the pathogenic fungus *M. grisea* by following the changing growth of this fungus in the presence of various concentrations of inhibitor, in various culture media and over a period of 7 days.

200 μl of culture medium, minimum medium (MM) or minimum medium+leucine, valine and isoleucine at 0.3 mM (MM+ILV), is inoculated with a suspension of spores of the *M. grisea* strain P1.2 at a final concentration of $10^5$ spores/ml. The microplate is incubated at ambient temperature and the optical density at 630 nm ($OD_{630}$) is measured on days 0, 3, 4, 5, 6 and 7 (D0, D3, D4, D5, D6 and D7). The optical density provides a measurement of the growth of the mycelium.

Figure 3:
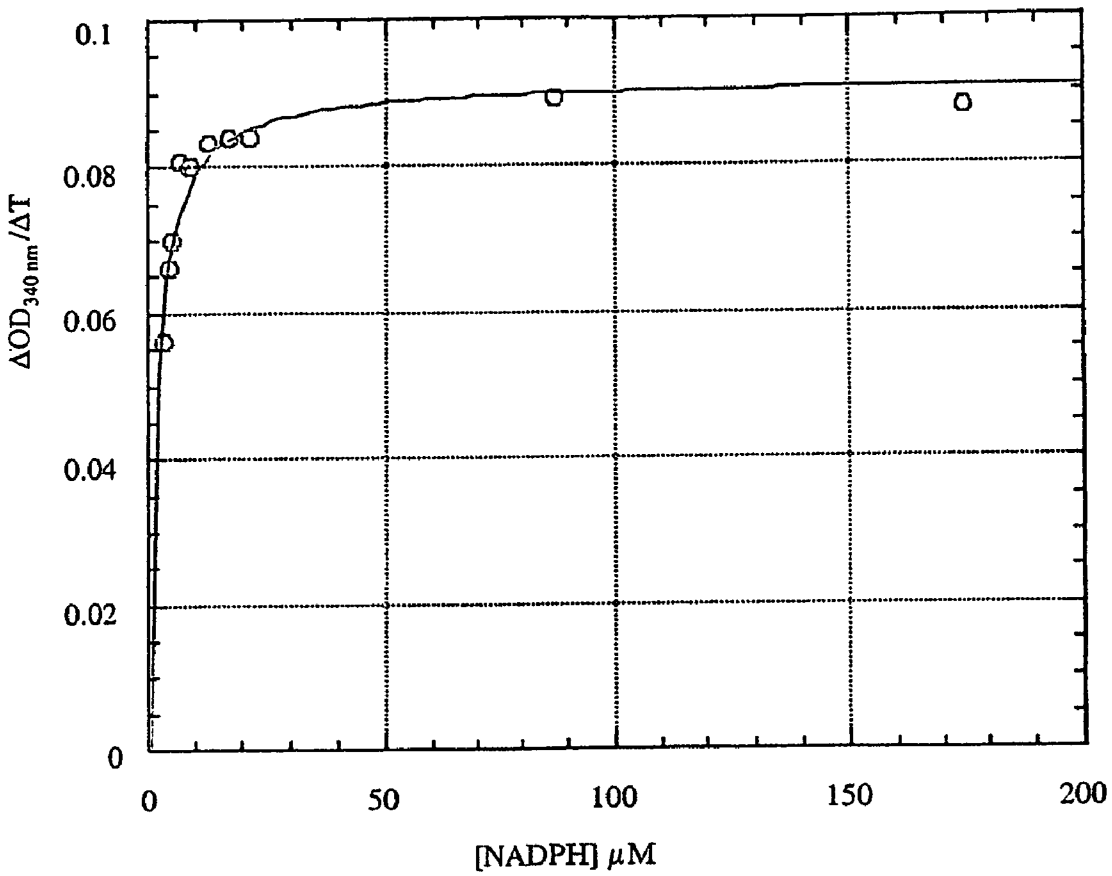

FIG. 3: Influence of the concentration of NADPH on the enzyme activity of the yeast reductoisomerase. The enzyme activity measurements are carried out at 25° C. in 1 ml of the following reaction medium: 10 mM $MgCl_2$, from 0 to 175 μM NADPH, 0.48 mM AHB, and in 50 mM sodium Hepes buffer, pH 7.5. The curve is Michaelis Menten model-adjusted. The $K_M$ for NADPH is 1.6 μM.

FIGS. 4A and 4B: Influence of the concentration of substrate AHB [A] and AL [B] on the enzyme activity of the yeast reductoisomerase. The enzyme activity measurements are carried out at 25° C. in the following reaction medium: 10 mM $MgCl_2$, 250 μM NADPH and in 1 ml of 50 mM sodium Hepes buffer, pH 7.5 and in the presence of AHB [A] and of AL [B]. The curves are Michaelis Menten model-adjusted. A The $K_M$ for AHB is 104 μM. B The $K_M$ for AL is 266 μM.

Figure 5:
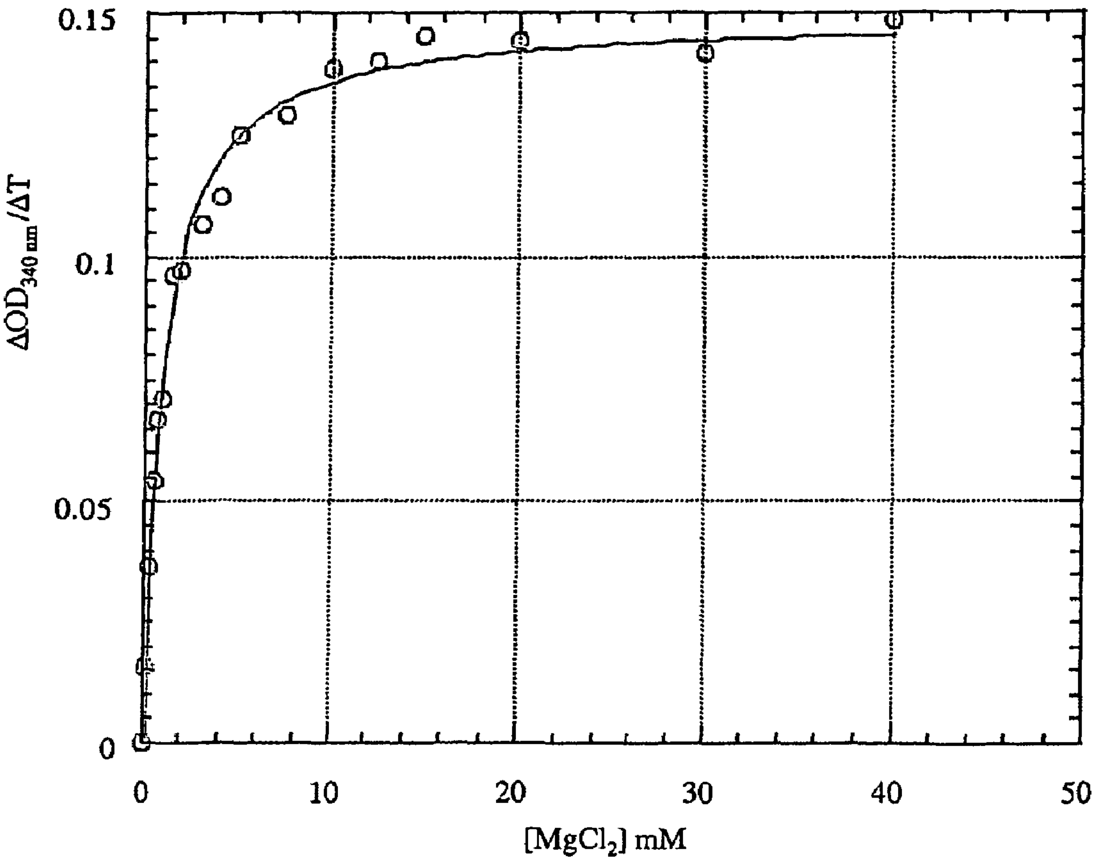

FIG. 5: Influence of the concentration of magnesium on the enzyme activity of the yeast reductoisomerase. The enzyme activity measurements are carried out at 25° C. in 1 ml of the following reaction medium: from 0 to 40 mM of $MgCl_2$, 250 μM NADPH, 0.48 mM AHB, and 50 mM sodium Hepes buffer, pH 7.5. The curve is Michaelis Menten model-adjusted. The $K_M$ for the $Mg^{2+}$ is 968 μM.

FIGS. 6A and 6B: Stoichiometry for binding of the inhibitors dimethylphosphinoyl-2-hydroxyacetate and N-hydroxy-N-isopropyloxamate to the yeast reductoisomerase. The inhibitors Hoe 704 [A] and IpOHA [B] (0.1 nmol) are incubated with varying amounts of enzyme (0 to 0.4 nmol) for 20 minutes at 25° C. with 25 nmol of NADPH and 0.25 μmol of $Mg^{2+}$ in a volume of 10 μl. The enzyme activity measurements are carried out at 25° C. in 1 ml of the following reaction medium: 10 mM $MgCl_2$, 250 μM NADPH, 0.48 mM AHB, and in 50 mM sodium Hepes buffer, pH 7.5.

FIGS. 7A and 7B: Kinetics of inhibition of the yeast reductoisomerase in the presence of the inhibitors dimethylphosphinoyl-2-hydroxyacetate [A] and N-hydroxy-N-isopropyloxamate [B]. The enzyme activity measurements are carried out at 25° C. in 1 ml of the following reaction medium: 10 mM $MgCl_2$, 250 μM NADPH, 0.48 mM AHB in 50 mM sodium Hepes buffer, pH 7.5, and in the presence of enzyme 110 nM.

The reactions are initiated by simultaneously adding varying amounts of inhibitors dimethylphosphinoyl-2-hydroxyacetate [A] and N-hydroxy-N-isopropyloxamate [B] (from 2 μM to 30 μM) to the reaction medium. The curves are plotted according to the equation (1), which makes it possible to determine the values for $K_{obs}$, the apparent rate of formation of the enzyme-inhibitor complex.

FIGS. 8A and 8B: Kinetics of inhibition of the yeast reductoisomerase in the presence of the inhibitors dimethylphosphinoyl-2-hydroxyacetate [A] and N-hydroxy-N-isopropyloxamate [B]. The enzyme activity measurements are carried out at 25° C. in 1 ml of the following reaction medium: 10 mM $MgCl_2$, 250 μM NADPH, 0.48 mM AHB in 50 mM sodium Hepes buffer, pH 7.5, and in the presence of enzyme at 110 nM.

The reactions are initiated by simultaneously adding varying amounts of inhibitors [A] and [B] (from 2 μM to 50 μM) to the reaction medium.

FIGS. 9A and 9B: Determination of the association constant $k_0$ for the dimethylphosphinoyl-2-hydroxyacetate [A] and for the N-hydroxy-N-isopropyloxamate [B] on the yeast reductoisomerase using the representation 1/Kobs as a function of the concentration of substrate AHB. The enzyme activity measurements are carried out at 25° C. in 1 ml of the following reaction medium: 10 mM $MgCl_2$, 250 μM NADPH, from 125 μM to 2.375 mM AHB, and in 50 mM sodium Hepes buffer, pH 7.5, and in the presence of enzyme at 110 nM. The reactions are initiated by simultaneously adding varying amounts of substrate AHB (from 125 μM to 2.375 mM) and the inhibitors [A] (10 μM) and [B] (15 μM) to the reaction medium.

The curves are plotted according to the equation (3), which makes it possible to determine the values for $k_0$, the rate of association of the inhibitor with the enzyme.

DESCRIPTION OF THE SEQUENCE LISTING

SEQ ID NO:1: *Magnaporthe grisea* ketol-acid reductoisomerase.

SEQ ID NO:2: *Saccharomyces cerevisiae* ketol-acid reductoisomerase.

SEQ ID NO:3: *Neurospora crassa* ketol-acid reductoisomerase.

SEQ ID NO:4: *Magnaporthe grisea* ketol-acid reductoisomerase gene cDNA.

SEQ ID NO:5: *Magnaporthe grisea* ketol-acid reductoisomerase.

SEQ ID NO:6: *Magnaporthe grisea* ketol-acid reductoisomerase gene.

SEQ ID NOS:7–18: Primers for PCR.

DESCRIPTION OF THE INVENTION

A subject of the present invention is methods for treating crops against fungal diseases by applying an effective amount of a ketol-acid reductoisomerase inhibitor.

A subject of the invention is a method for combating, in a curative or preventive capacity, phytopathogenic fungi affecting crops, characterized in that an effective (agronomically effective) and nonphytotoxic amount of a ketol-acid reductoisomerase inhibitor is applied to the soil where the plants are growing or where they are likely to grow, to the leaves and/or the fruits of the plants or to the seeds of the plants. The expression "effective and nonphytotoxic amount" is intended to mean an amount of inhibitor which is sufficient to control or destroy the fungi present or likely to appear on the crops, and which does not result in any appreciable symptom of phytotoxicity for said crops. Such an amount can vary within a wide range depending on the fungus to be combated, the type of crop, the climatic conditions and the compounds included in the fungicidal composition according to the invention. This amount can be determined by systematic field trials, which are within the scope of those skilled in the art.

The methods according to the invention are useful for treating the seeds of cereals (wheat, rye, triticale and barley in particular), of potato, of cotton, of pea, of rapeseed, of maize or of flax, or else the seeds of forest trees, or else genetically modified seeds of these plants. The present invention also relates to foliar application to the plant crops, i.e. to the foliage, the flowers, the fruits and/or the trunks of the plants concerned. Among the plants targeted by the methods according to the invention, mention may be made of rice, maize, cotton, cereals, such as wheat, barley or triticale, fruit trees, in particular apple trees, pear trees, peach trees, grapevine, banana trees, orange trees, lemon trees, etc., oil-producing crops, for example rapeseed or sunflower, market-garden and vegetable crops, tomatoes, salads, protein-producing crops, pea, Solanaceae, for example potato, beetroot, flax, and forest trees, and also genetically modified homologues of these crops.

Among the plants targeted by the method according to the invention, mention may be made of:

- wheat, as regards combating the following seed diseases: fusaria (*Microdochium nivale* and *Fusarium roseum*), stinking smut (*Tilletia caries, Tilletia controversa* or *Tilletia indica*), septoria disease (*Septoria nodorum*); loose smut (*Ustilago tritici*);
- wheat, as regards combating the following diseases of the parts of the plant above ground: cereal eyespot (*Tapesia yallundae, Tapesia acuiformis*), take-all (*Gaeumannomyces graminis*), foot blight (*F. culmorum, F. graminearum*), head blight (*F. culmorum, F. graminearum, Microdochium nivale*), black speck (*Rhizoctonia cerealis*), powdery mildew (*Erysiphe graminisforma* specie tritici), rusts (*Puccinia striiformis* and *Puccinia recondita*) and *septoria* diseases (*Septoria tritici* and *Septoria nodorum*), net blotch (*Drechslera tritici-repentis*);
- barley, as regards combating the following seed diseases: net blotch diseases (*Pyrenophora graminea, Pyrenophora teres* and *Cochliobolus sativus*), loose smut (*Ustilago nuda*) and fusaria (*Microdochium nivale* and *Fusarium roseum*);
- barley, as regards combating the following diseases of the parts of the plant above ground: cereal eyespot (*Tapesia yallundae*), net blotch diseases (*Pyrenophora teres* and *Cochliobolus sativus*), powdery mildew (*Erysiphe graminis form a specie hordei*), dwarfleaf rust (*Puccinia hordei*) and leaf blotch (*Rhynchosporium secalis*);
- potato, as regards combating tuber diseases (in particular *Helminthosporium solani, Phoma tuberosa, Rhizoctonia solani, Fusarium solani*), and mildew (*Phytopthora infestans*);
- potato, as regards combating the following foliage diseases: early blight (*Alternaria solani*), mildew (*Phytophthora infestans*);
- cotton, as regards combating the following diseases of young plants grown from seeds: damping-off and collar rot (*Rhizoctonia solani, Fusarium oxysporum*), black root rot (*Thielaviopsis basicola*);

protein-producing crops, for example pea, as regards combating the following seed diseases: anthracnose (*Ascochyta pisi, Mycosphaerella pinodes*), fusaria (*Fusarium oxysporum*), gray mold (*Botrytis cinerea*), mildew (*Peronospora pisi*);

oil-producing crops, for example rapeseed, as regards combating the following seed diseases: *Phoma lingam, Alternaria brassicae* and *Sclerotinia sclerotiorum;* maize, as regards combating seed diseases: (*Rhizopus* sp., *Penicillium* sp., *Trichoderma* sp., *Aspergillus* sp. and *Gibberella fujikuroi*);

flax, as regards combating seed diseases: *Alternaria linicola;* forest trees, as regards combating damping-off (*Fusarium oxysporum, Rhizoctonia solani*);

rice, as regards combating the following diseases of the parts above ground: blast disease (*Magnaporthe grisea*), black speck (*Rhizoctonia solani*);

vegetable crops, as regards combating the following diseases of seedlings or of young plants grown from seeds: damping-off and collar rot (*Fusarium oxysporum, Fusarium roseum, Rhizoctonia solani, Pythium* sp.);

vegetable crops, as regards combating the following diseases of the parts above ground:

gray mold (*Botrytis* sp.), powdery mildews (in particular *Erysiphe cichoracearum, Sphaerotheca fuliginea, Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example, *Bremia lactucae, Peronospora* sp., *Pseudoperonospora* sp, *Phytophthora* sp);

fruit trees, as regard diseases of the parts above ground: monilia disease (*Monilia fructigenae, M. laxa*), scab (Venturia inaequalis), powdery mildew (Podosphaera leucotricha);

grapevine, as regards foliage diseases: in particular gray mold (*Botrytis cinerea*), powdery mildew (*Uncinula necator*), black rot (*Guignardia biwelli*), mildew (*Plasmopara viticola*);

beetroot, as regards the following diseases of the parts above ground: cercosporia blight (*Cercospora beticola*), powdery mildew (*Erysiphe beticola*), leaf spot (*Ramularia beticola*).

Ketol-acid reductoisomerase is a well-characterized enzyme which is found in plants and microorganisms (bacteria, yeast, fungi). The methods of the present invention use ketol-acid reductoisomerase inhibitors. In a present embodiment, the invention relates to the use of inhibitors of fungal ketol-acid reductoisomerase, more preferably of inhibitors of the ketol-acid reductoisomerase of a phytopathogenic fungus, for treating fungal diseases affecting crops. In a particular embodiment of the invention, the ketol-acid reductoisomerase inhibitors inhibit the ketol-acid reductoisomerase of *Magnaporthe grisea* and/or of *Saccharomyces cerevisiae* and/or of *Neurospora crassa*. In another particular embodiment, the ketol-acid reductoisomerase inhibitor is an inhibitor of the enzyme activity of the ketol-acid reductoisomerase of SEQ ID NO:1, of SEQ ID NO:2, of SEQ ID NO:3 and/or of SEQ ID NO:5.

Any ketol-acid reductoisomerase inhibitor can be used in the methods according to the invention. Ketol-acid reductoisomerase inhibitors are well known to those skilled in the art, and these inhibitors have in particular been described in EP106114; U.S. Pat. No. 4,594,098, EP196026, EP481407, WO 94/23063, CA2002021 and WO 97/37660.

In a particular embodiment of the invention, the ketol-acid reductoisomerase inhibitor is a reaction intermediate analog which binds to the active site of the ketol-acid reductoisomerase.

Preferably, the ketol-acid reductoisomerase inhibitor is dimethylphosphinoyl-2-hydroxyacetate.

More preferably, the ketol-acid reductoisomerase inhibitor is N-hydroxy-N-isopropyloxamate.

In a preferred embodiment of the invention, the ketol-acid reductoisomerase inhibitor is in the form of a fungicidal composition. The invention also relates to fungicidal compositions comprising an effective amount of at least one ketol-acid reductoisomerase inhibitor. The fungicidal compositions according to the invention comprise, besides the inhibitor, agriculturally acceptable solid or liquid carriers and/or surfactants which are also agriculturally acceptable. The usual inert carriers and the usual surfactants can in particular be used. These fungicidal compositions according to the invention can also contain any type of other ingredients, such as, for example, protective colloids, adhesives, thickeners, thixotropic agents, penetrating agents, stabilizers, sequestering agents, etc. More generally, the ketol-acid reductoisomerase inhibitors can be combined with all the solid or liquid additives corresponding to the conventional techniques of formulation.

A subject of the present invention is also fungicidal compositions comprising a ketol-acid reductoisomerase inhibitor and another fungicidal compound. Mixtures with other fungicides are particularly advantageous, in particular mixtures with acibenzolar-S-methyl, azoxystrobin, benalaxyl, benomyl, blasticidin-S, bromuconazole, captafol, captan, carbendazim, carboxin, carpropamide, chlorothalonil, fungicidal compositions based on copper, or on copper derivatives such as copper hydroxide or copper oxychloride, cyazofamide, cymoxanil, cyproconazole, cyprodinil, dichloran, diclocymet, dichloran, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamid, fenpiclonil, fenpropidine, fenpropimorph, ferimzone, fluazinam, fludioxonil, flumetover, fluquinconazole, flusilazole, flusulfamide, flutolanil, flutriafol, folpet, furalaxyl, furametpyr, guazatine, hexaconazole, hymexazol, imazalil, iprobenphos, iprodione, isoprothiolane, kasugamycin, kresoxim-methyl, mancozeb, maneb, mefenoxam, mepanipyrim, metalaxyl and its entiomeric forms such as metalaxyl-M, metconazole, metiram-zinc, metominostrobin, oxadixyl, pefurazoate, penconazole, pencycuron, phosphoric acid and its derivatives such as fosetyl-Al, phthalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, tebuconazole, tetraconazole, thiabendazole, thifluzamide, thiophanate, e.g. thiophanate-methyl, thiram, tridimefon, triadimenol, tricyclazole, tridemorph, trifloxystrobin, triticonazole, derivatives of valinamide such as, for example, iprovalicarb, vinclozolin, zineb and zoxamide. The mixtures thus obtained have a wider spectrum of activity. The compositions according to the invention may also comprise one or more insecticides, bactericides or acaricides or pheromones or other compounds having a biological activity.

The subject of the present invention is also methods for producing a fungicidal composition using a ketol-acid reductoisomerase inhibitor.

The subject of the present invention is also methods for preparing fungicidal compounds, comprising identifying compounds which inhibit the enzyme activity of ketol-acid reductoisomerase.

The enzyme reaction is carried out in the presence of the test compound in order to measure the inhibition of the enzyme activity of the ketol-acid reductoisomerase. All biochemical assays for measuring the enzyme activity of ketol-acid reductoisomerase and therefore for identifying compounds which inhibit this enzyme activity can be used in the methods according to the invention. The biochemical assays are well known to those skilled in the art (Dumas et al., *Biochem. J.* 288:865–874, 1992; Dumas et al., *Biochem. J.* 301:813–820, 1994; Dumas et al., *Febs Letters* 408: 156–160, 1997, Halgand et al., Biochemistry 37:4773–4781, 1998, Wessel et al., *Biochemistry* 37:12753–12760, 1998; Halgand et al., *Biochemistry* 38:6025–6034, 1999).

The enzyme reactions are advantageously carried out in solution in a suitable buffer. The use of this type of reaction medium makes it possible to perform a large number of reactions in parallel and therefore to test a large number of compounds in a microplate format, for example.

Preferably, the methods for identifying compounds which inhibit the enzyme activity of ketol-acid reductoisomerase comprise bringing these compounds into contact with the ketol-acid reductoisomerase in the presence of magnesium, of NADPH in the substrate, and measuring this enzyme activity.

Advantageously, in the methods according to the invention, measurement of the enzyme activity comprises measuring the decrease in absorption of NADPH at 340 nm, and the substrate used for the enzyme reaction is 2-acetolactate (AL) or 2-aceto-2-hydroxybutyrate (AHB). It is understood that any other method for measuring enzyme activity known to those skilled in the art may be used in the methods according to the invention.

Any ketol-acid reductoisomerase can be used in the methods according to the invention. Ketol-acid reductoisomerases have been characterized in several organisms, such as plants, bacteria, yeast and fungi. The corresponding genes have been cloned, making it possible to determine the protein sequence of this enzyme (Dumas et al., *Biochem. J.* 277:69–475, 1991; Curien et al., *Plant Mol. Biol.* 21:717–722, 1993; Dumas et al., *Biochem. J.* 294:821–828, 1993; Biou et al., *EMBO J.* 16:3405–3415, 1997; Dumas et al., *Biochemistry* 34:6026–6036, 1995; Dumas et al., *Accounts of Chemical Research* 34:399–408, 2001; Sista et al., *Gene,* 120:115–118, 1992; Zelenaya-Troitskaya et al., *EMBO J.* 14:3268–3276, 1995).

In a preferred embodiment of the invention, the ketol-acid reductoisomerase used in the methods according to the invention is represented in SEQ ID NO: 1, in SEQ ID NO:2, in SEQ ID NO:3 and/or in SEQ ID NO:5.

Preferably, the ketol-acid reductoisomerase is isolated, purified or partially purified form its natural environment. The ketol-acid reductoisomerase can be prepared using various methods. These methods are in particular purification from natural sources such as cells naturally expressing these polypeptides, production of recombinant polypeptides by appropriate host cells and subsequent purification thereof, production by chemical synthesis or, finally, a combination of these various approaches. These various methods of production are well known to those skilled in the art.

In a first embodiment of the invention, the ketol-acid reductoisomerase is purified from an organism which naturally produces this enzyme, such as, for example, bacteria such as *E. coli*, yeasts such as *S. cerevisiae*, or fungi such as *N. crassa* or *M. grisea*.

In a preferred embodiment of the invention, the ketol-acid reductoisomerase is overexpressed in a recombinant host organism. The methods for engineering DNA fragments and the expression of polypeptides in host cells are well known to those skilled in the art and have, for example, been described in "Current Protocols in Molecular Biology" Volumes 1 and 2, F. M. Ausubel et al., published by Greene Publishing Associates and Wiley-Interscience (1989) or in Molecular Cloning, T. Maniatis, E. F. Fritsch, J. Sambrook (1982).

Preferably, the methods for identifying compounds which inhibit the enzyme activity of ketol-acid reductoisomerase comprise expressing the ketol-acid reductoisomerase in the host organism, purifying the ketol-acid reductoisomerase produced by the host organism, bringing these compounds into contact with the purified ketol-acid reductoisomerase in the presence of magnesium, of NADPH and of substrate, and measuring the enzyme activity.

In a preferred embodiment, all these methods comprise an additional step in which it is determined whether said compounds which inhibit the enzyme activity of the ketol-acid reductoisomerase inhibit fungal growth and/or pathogenesis.

The present invention therefore relates to methods for identifying compounds which inhibit fungal growth and/or pathogenesis by inhibiting the enzyme activity of ketol-acid reductoisomerase. These methods consist in subjecting a compound, or a mixture of compounds, to an appropriate assay for identifying the ketol-acid reductoisomerase-inhibiting compounds and in selecting the compounds which react positively to said assay, where appropriate in isolating them, and then in identifying them.

Preferably, the appropriate assay is an assay for the enzyme activity of the ketol-acid reductoisomerase as defined above.

Preferably, a compound identified according to these methods is then tested for its antifungal properties and for its ability to inhibit the pathogenesis and/or the growth of the fungus for plants, according to methods known to those skilled in the art. Preferably, the compound is evaluated using phenotypic tests such as pathogenesis assays on leaves or on whole plants.

According to the invention, the term "compound" is intended to mean any chemical compound or mixture of chemical compounds, including peptides and proteins.

According to the invention, the term "mixture of compounds" is understood to mean at least two different compounds, such as, for example, the (dia)stereoisomers of a molecule, mixtures of natural origin derived from the extraction of biological material (plants, plant tissues, bacterial cultures, yeast cultures or fungal cultures, insect, animal tissues, etc.) or unpurified or totally or partially purified reaction mixtures, or else mixtures of products derived from combinatorial chemistry techniques.

Finally, the present invention relates to novel fungal pathogenesis-inhibiting compounds which inhibit the enzyme activity of ketol-acid reductoisomerase, in particular the compounds identified by the methods according to the invention and/or the compounds derived from the compounds identified by the methods according to the invention.

Preferably, the fungal pathogenesis-inhibiting compounds which inhibit the enzyme activity of ketol-acid reductoisomerase are not general enzyme inhibitors. Also preferably, the compounds according to the invention are not compounds already known to have fungicidal activity and/or activity on fungal pathogenesis.

A subject of the invention is also a method for treating plants against a phytopathogenic fungus, characterized in that it comprises treating said plants with a compound identified by a method according to the invention.

The present invention also relates to a method for preparing a fungal pathogenesis-inhibiting compound, said method comprising the steps consisting in identifying a fungal pathogenesis-inhibiting compound which inhibits the enzyme activity of ketol-acid reductoisomerase by the method of identification according to the invention, and then in preparing said identified compound by the usual methods of chemical synthesis, of enzymatic synthesis and/or of extraction of biological material. The step for preparing the compound can be preceded, where appropriate, by an "optimization" step by which a compound derived from the compound identified by the method of identification according to the invention is identified, said derived compound then being prepared by the usual methods.

EXAMPLES

Example 1

Cloning of the *Manaporthe grisea* ILV5 Gene

An internal fragment of the *M. grisea* ILV5 gene was amplified by PCR from the genomic DNA of this fungus using pairs of degenerate primers corresponding to protein domains which are conserved between fungal reductoisomerases. The PCR product obtained was then cloned into the plasmid pGEM®-T-Easy (Promega), sequenced, and amplified by PCR with a new pair of primers. The latter PCR product was used as a homologous probe for screening an *M. grisea* cosmid DNA library. The sequence of the *M. grisea* ILV5 gene was then produced using one of the positive clones and oligonucleotides derived from the sequence of the PCR product already obtained.

1.1. Isolation of an Internal Fragment of the *M. grisea* ILV5 Gene by Amplification Using Degenerate Oligonucleotides 1.1.1 Choice of Degenerate Oligonucleotides Amplification of an internal fragment of the *N. grisea* ILV5 gene was carried out by PCR using degenerate oligonucleotides. These degenerate oligonucleotides were chosen based on comparison of the protein sequences of the reductoisomerases of *N. Crassa* and of *S. cerevisiae*. This comparison made it possible to demonstrate 4 domains which are conserved between these two fungal reductoisomerase sequences, which should be present in the reductoisomerase of *M. grisea*. These 4 conserved domains consist of a succession of at least 7 conserved amino acids. The sequence of the degenerate oligonucleotides was determined from that of the amino acids of the conserved domains translated according to the genetic code. In order for the degree of degeneracy (number of codons for a given amino acid) to be as low as possible, amino acids such as arginine, leucine or serine are to be avoided since six codons correspond thereto. The amino acids methionine and tryptophan are, for their part, desired, since a single codon corresponds thereto. The degree of degeneracy should also be low at the 3' end of the oligonucleotide, in order to increase the specificity of amplification. We were able to define four oligonucleotides: oligonucleotides 1(+) and 3(+) on the (+) strand; and oligonucleotides 2(−) and 4(−) on the (−) strand of the *M. grisea* DNA. Thus, the PCR amplification can be carried out with four different pairs of degenerate oligonucleotides: 1 (+) and 2(−); 1 (+) and 4(−); 3(+) and 2(−); 3(+) and 4(−).

1.1.2. Amplification of an Internal Fragment of the *M. grisea* ILV5 Gene Using Degenerate Oligonucleotides The optimum conditions for amplification of the *M. grisea* ILV5 gene were determined by varying the pair of primers and their hybridization temperature. The first three amplification cycles were carried out at a variable hybridization temperature (42° C., 50° C. or 55° C.), whereas the hybridization temperature for the other cycles is 55° C. Positive controls were performed with the genomic DNA of *N. crassa* and of *S. cerevisiae* under the same conditions as for the genomic DNA of *M. grisea*. At a hybridization temperature of 42° C., the *S. cerevisiae* DNA fragments were amplified at the expected size, i.e. 590 bp, 610 bp, 440 bp and 470 bp, with the pairs of primers (1-4), (1-2), (3-4) and (3-2), respectively. The amplification profiles for *S. cerevisiae* genomic DNA with the pairs of primers (1-4) and (3-2) are, however, complex. For a hybridization temperature of 50° C., *N. crassa* DNA fragments were amplified at the expected size, i.e. 660 bp, 685 bp, 523 bp and 544 bp, with the pairs of primers (1-4), (1-2), (3-2) respectively, although the amplification profiles with the pairs of primers (1-4) and (3-4) are complex. The various pairs of degenerate oligonucleotides made it possible to amplify a fragment of expected size from the yeast genomic DNA and from the *N. crassa* genomic DNA. These degenerate oligonucleotides could therefore be used to amplify the *M. grisea* ILV5 gene. The amount of oligonucleotides used, tested at a hybridization temperature of 42° C., does not appear to have any influence on the amplification of the *M. grisea* genomic DNA. At a hybridization temperature in the first PCR cycles of 42° C., the amplification profiles for the *M. grisea* genomic DNA, obtained with the various pairs of primers, are quite complex. At a hybridization temperature of 50° C., a simplification of the amplification profiles for the *M. grisea* genomic DNA was observed for most of the pairs of primers, in particular for the pair of primers (1-2) which makes it possible to amplify a single DNA fragment at the expected size (685 bp). A hybridization temperature in the first PCR cycles of 55° C. does not make it possible to increase the specificity of the amplification with the pairs of primers (1-2) and (3-2) and reduces its yield. The best conditions for amplification from the *M. grisea* genomic DNA were therefore obtained at a primer hybridization temperature in the first PCR cycles of 50° C., with the pair of oligonucleotides (1-2).

1.1.3. Cloning of a PCR-amplified Internal Fragment of the *M. grisea* ILV5 Gene, in the Plasmid pGEM®-T-easy The internal fragment of the *M. grisea* ILV5 gene was amplified by PCR from the *M. grisea* genomic DNA, with the pair of primers (1-2), at a primer hybridization temperature of 50° C. for 3 cycles, and then 55° C. for the other amplification cycles. This PCR product, of approximately 680 bp, is purified after separation by agarose gel electrophoresis and then cloned into the plasmid pGEM®-T-easy. The bacterial colonies obtained after transformation, and using a white/blue selection system (X-Gal), showed three different phenotypes: white, blue, and white with the center of the colony being blue (called white/blue colonies). 30 colonies of various phenotypes were analyzed by PCR using the universal primers Sp6 and T7, which hybridize on either side of the cloning site of the plasmid pGEM®-T-easy. The 20 white colonies and the 10 white/blue colonies are positive. In fact, from these colonies, a DNA fragment was amplified at the expected size (810 bp), which corresponds to the size of the insert (680 bp) plus the distance separating the insert from each of the primers Sp6 and T7 (129 bp). Two clones of different phenotypes, white and white/blue, were then chosen in order to be sequenced. These are clones no. 4 (white) and no. 20 (white/blue).

1.1.4. Analysis of the Sequence of the Cloned Internal Fragment of the *M. grisea* ILV5 Gene Comparison of the nucleotide sequences of the two clones no. 4 and no. 20 showed that they correspond to the same DNA fragment cloned in different orientations into the plasmid pGEM®-T-easy, which might explain their phenotypic difference (white and white/blue). The double-stranded nucleotide sequence of this cloned fragment was thus obtained. The homology of this nucleotide sequence with those encoding known proteins was sought using the BLASTX™ program from NCBI (National Center for Biotechnology Information). This program compares the translated sequences of the six reading frames of a nucleotide sequence with all the protein sequences contained in the databases. Significant homology between the nucleotide sequence of the cloned fragment and the protein sequence of the *N. crassa* reductoisomerase (error of e-102) was identified. The percentage amino acid identity within the region defined by the software for comparing these two sequences is 94%. The fragment cloned into the plasmid pGEM®-T-easy therefore corresponds to the internal fragment of the *M* grisea ILV5 gene. Although the sequence of the internal fragment of the *M. grisea* ILV5 gene and that of the *N. crassa* ILV5 gene exhibits strong homology, a difference exists at the center of the sequence of the *M. grisea* ILV5 gene. This difference might correspond to the presence of an intron within the *M. grisea* sequence, since a 77 bp intron exists in *N. crassa* at this position. The position in the sequence of this intron was sought. A 5' splicing consensus motif was identified in the nucleotide sequence of the internal fragment of the *M. grisea* ILV5 gene, along with a 3' splicing consensus motif and a lariat sequence. The putative intron (86 bp) of the internal fragment of the *M. grisea* ILV5 gene was therefore identified. Splicing of the intron of the sequence of the internal fragment of the *M. grisea* ILV5 gene made it possible to obtain a "theoretical" cDNA fragment. The fragment of the protein sequence of the *M. grisea* reductoisomerase then deduced from this "theoretical" cDNA was compared with that of the *N. crassa* reductoisomerase, showing very strong identity between the primary sequences of these two enzymes (FIG. 1).

1.2. Screening of an *M. grisea* Cosmid Library with a Probe for the *M. grisea* ILV5 Gene 1.2.1. Construction of the Homologous Probe for the *M. grisea* ILV5 Gene An internal fragment of the *M. grisea* ILV5 gene was amplified by PCR, from clone no. 4, using the primers 13U and 549L defined on the basis of the sequence of the ILV5 gene cloned into the plasmid pGEM®-T-easy. This fragment, after purification on agarose gel, was used as a matrix to prepare a labeled probe for the ILV5 gene.

1.2.2. Screening of the *M. grisea* Guy 11 Cosmid Library by PCR Using Primers Specific for the *M. grisea* ILV5 Gene The Guy11 cosmid library is represented in the form of 28 pools of 96 DNA mini preparations corresponding to the 96 different cosmids present in a 96-well plate (2688 clones). The *M. grisea* ILV5 gene was sought in this cosmid library by performing a PCR amplification on these pools of DNA mini preparations using the primers 300U and 549L defined on the basis of the known sequence of the ILV5 gene. A fragment of expected size (249 bp) was amplified from the pools no. 17; 19; 20; 21; 27; 28 and 29. The search for the ILV5 gene was continued by hybridizing, with the probe for the ILV5 gene, the cosmids from plates no. 17; 19; 20; 21; 27; 28 and 29.

1.2.3. Screening of the *M. grisea* Guy11 Cosmid Library by Hybridization with the Homologous Probe for the *M. grisea* ILV5 Gene The bacterial colonies derived from plates no. 17; 19; 20; 21; 27; 28 and 29 were replicated on nylon membranes and hybridized with the probe for the *M. grisea* ILV5 gene. This hybridization made it possible to select the cosmids G6 and A7 from plates no. 20 and 27, respectively, and the cosmids B5 and B6 from plate no. 29.

1.2.4. Characterization of the *M. grisea* ILV5 Gene Using The Cosmid 20/G6

(a) Sequencing of the *M. grisea* ILV5 Gene Using the Cosmid 20/G6

The sequencing of the ILV5 gene was carried out in steps. The first sequencing reaction was carried out using divergent primers chosen from the known sequence of the internal fragment of the *M. grisea* ILV5 gene obtained by PCR. Based on this new ILV5 gene sequence, further primers were defined in order to carry out other sequencing reactions, until the *M. grisea* ILV5 gene had been entirely sequenced. The sequences translated from the entire nucleotide sequence of the ILV5 gene according to the six reading frames were compared with the protein sequence of the *N. crassa* reductoisomerase; in order to locate the position of the translation-initiating ATG, of the translation-terminating stop codon, and of the various possible introns. Thus, the translation-initiating ATG was identified on the nucleotide sequence of the ILV5 gene and serves as reference (+1) from which the other elements of the sequence are positioned. Three putative introns were located in the nucleotide sequence of the *M. grisea* ILV5 gene. The first intron is thought to be located between positions (in bp) 199 and 280, the second intron at position 314–390 and the third intron is thought to be located between positions 670 and 755 of the *M. grisea* ILV5 gene. The translation-terminating stop codon is thought to be at position 1449 of the sequence of the *M. grisea* ILV5 gene. Isolation of the cDNA of the *M. grisea* ILV5 gene was undertaken in order to verify the position of the suspected introns by comparison of the protein sequences of *M. grisea* and of *N. crassa.*

(b) Isolation of the cDNA of the *M. grisea* ILV5 Gene and Search for the Introns of the *M. grisea* Gene The cDNA of the *M. grisea* ILV5 gene was isolated by carrying out a PCR amplification from a cDNA library of the isolate P1.2 (RNA of mycelium cultured in complete medium) using the oligonucleotides defined on the basis of the ILV5 gene sequence: oligonucleotides 22U and 1603L. Oligonucleotide 22U is located before the translation-initiating ATG and oligonucleotide 1603L is located 93 bp after the translation-terminating STOP codon. Two fragments are amplified with this pair of primers: a fragment less than 500 bp in size and a fragment amplified at the expected size, i.e. 1.6 kb. The fragment amplified at the expected size is purified after separation by agarose gel electrophoresis and cloned into the plasmid pGEM®-T-easy. The 24 bacterial clones obtained after transformation are analyzed by PCR using the pair of primers 22U and 1603L. These 24 clones possess the cDNA of the *M. grisea* ILV5 gene, since a DNA fragment was in fact amplified at the expected size (1.6 kb). Clone no. 18 was chosen in order to be sequenced using the universal primers Sp6 and T7. Comparison of the nucleotide sequence of the cDNA of the ILV5 gene allowed us to determine the exact position of the introns. The three introns are located at the positions predicted by the comparison of the protein sequences of the N. crassa reductoisomerases and of the translations of the *M. grisea* ILV5 gene. In N. crassa, the ILVS gene has 4 introns which are positioned differently and are different in length compared to the *M. grisea* ILV5 gene.

(c) Protein Sequence of the *M. grisea* Reductoisomerase, Deduced from All the Data Acquired on the *M. grisea* ILV5 Gene The protein sequence of the *M. grisea* ILV5 gene was deduced from the cDNA sequence of this gene. Comparison of the protein sequences of the reductoisomerases of *M. grisea*, of *N. crassa* and of *S. cerevisiae* shows very strong identity between the reductoisomerases of these three species. In fact, the percentage identity between the sequences of the *M. grisea* and *N. crassa* reductoisomerases is 86%. The percentage identity between the *M. grisea* and yeast reductoisomerases is 70%, and that between the *N. crassa* and yeast reductoisomerases is 72% (FIG. 1). *N. crassa* and *M. grisea* are very similar fungal species (pyrenomycetes), which might explain the high percentage identity between the reductoisomerases of these two species.

(d) Study of the Expression of the *M. grisea* Reductoisomerase in this Fungus Subjected to Various Conditions of Stress

*M. grisea* total RNA originating from a mycelium subjected to various conditions of stress was extracted and then transferred onto a membrane before being hybridized with the homologous probe for the *M. grisea* ILV5 gene. The ILV5 gene is expressed constitutively. It is thus expressed at the same level during a hyperosmotic stress or a nitrogen-based nutritional deficiency for an induction by cAMP, a thermal shock or an oxidative stress. It is not, however, expressed during a carbon-based nutritional deficiency.

Example 2

Disruption of the *Magnaporthe grisea* ILV5 Gene

After isolation and characterization of the ILV5 gene, the aim was to obtain mutants of the *M. grisea* ILV5 gene in order to test their pathogenic potency. The technique used to disrupt the ILV5 gene is insertional mutagenesis by transposition in vitro.

2.1. Subcloning of the *M. grisea* ILV5 Gene in the Plasmid pBC SK+

The subcloning of the ILV5 gene is carried out in the plasmid pBC SK+ before transposon-based insertional mutagenesis. The cosmid 20/G6 containing the ILV5 gene carries a gene for resistance to ampicillin; it cannot therefore be used directly as a target for the insertional mutagenesis. In fact, a double selection with kanamycin and ampicillin would not be selective enough for the target plasmids which have integrated the transposon, since the transposon-donating plasmid ($pGPS_3$ Hygro$^R$) is also resistant to kanamycin and to ampicillin. The ILV5 gene was therefore subcloned into a plasmid carrying a gene for resistance to chloramphenicol, the plasmid pBC SK+. The clones which have integrated the transposon into the target plasmid (pBC SK+ carrying the ILV5 gene) may be selected for their double resistance to kanamycin and to chloramphenicol. In addition, the size of the cosmid insert is too large (40 kb). A fragment of approximately 15 kb containing the ILV5 gene, subcloned into the plasmid pBC SK+, was chosen. In fact, the probability that the transposon will integrate into the ILV5 gene is greater when the size of the fragment carrying the ILV5 gene is decreased. The ILV5 gene is approximately 3 kb long, the probability that the transposon will integrate into the gene present in the cosmid (46 kb) is 6.5%, whereas the probability of integration of the transposon into the ILV5 gene subcloned into the plasmid pBC SK+ (18 kb) is approximately 3 times higher, i.e. approximately 17%. Subcloning of the genomic DNA fragment carrying the ILV5 gene was carried out by positioning this gene at the center of the insert. This type of construct facilitates integration of the mutated ILV5 gene into the *M. grisea* genome by homologous recombination. Mapping of the region of the cosmid 20/G6 carrying ILV5 made it possible to choose a 15 kb ClaI-ClaI fragment in which the ILV5 gene is relatively well centered. In fact, the ILV5 gene is ordered in the 5' position by 5 kb of the genomic sequence and in the 3' position by 5.5 kb. After digestion of the cosmid 20/G6 with ClaI, the 15 kb fragment containing the ILV5 gene was purified after separation on agarose gel and subcloned into the plasmid pBC SK+. Twenty-four colonies obtained after transformation were analyzed by PCR using the pair of primers 22U and 1603L specific for the ILV5 gene. The 5 clones amplify a fragment at the expected size (1.6 kb) possessing the ILV5 gene. Clone no. 19 was chosen to perform the in vitro transposition-based insertional mutagenesis of the ILV5 gene.

2.2. In vitro Transposition-Based Insertional Mutagenesis of the *M. grisea* ILV5 Gene The in vitro transposition-based insertional mutagenesis of the *M. grisea* ILV5 gene was carried out with the GPS™ (New England Biolabs) using clone no. 19. The plasmid $pGPS_3$ Hygro$^R$, which carries a gene for resistance to kanamycin and to hygromycin in the transprimer, is used as transposon donor. The plasmid pBC SK+, carrying the ILV5 gene and the gene for resistance to chloramphenicol, corresponds to the target plasmid. Once the insertional mutagenesis has been carried out, thermocompetent DH5α bacteria or electrocompetent DH10B bacteria are transformed with the "mutagenesis mixture". After transformation, the bacterial clones possessing an integration of the transposon in the target plasmid pBC SK+ are selected by virtue of their resistance both to kanamycin and chloramphenicol. This double resistance could also be conferred on the bacterial clones having both the target plasmid and the donor plasmid intact. Destruction of the donor plasmid by digestion with the P1-SceI enzyme makes it possible to overcome this problem. In order to determine whether the transposon has integrated into the *M. grisea* ILV5 gene, the selected bacterial clones are analyzed by PCR using the pair of primers 22U and 1603L, located on either side of the coding region of the ILV5 gene. Specifically, when the transposon Tn7 inserts into the ILV5 gene, there is no amplification with the pair of primers 22U and 1603L since the size of the DNA fragment located between these two primers is too great to be amplified (4.3 kb). This size corresponds to the sum of the size of the coding region of the *M. grisea* ILV5 gene (1.6 kb) and of the Tn7 transposon of 2.7 kb. After transformation of the thermocompetent DH5 cells, an absence of amplification was observed for 4 colonies (clones no. 3; 4; 8; 18) out of 32 colonies tested (12.5%). These bacterial clones therefore possess an insertion of the transprimer into the ILV5 gene. After transformation of the electrocompetent DH10B cells, out of 38 colonies tested by PCR, just one (2.6%) exhibits an absence of amplification (clone no. 29). Bacterial clones no. 3; 8; 18 and 29 were sequenced using divergent primers Tn7L and Tn7R located at each end of the transposon, in order to locate the exact position of the site of insertion of the Tn7 transposon within the sequence of the ILV5 gene. The transposon became integrated 21 bp before the ATG for clone no. 18, 9 bp after the ATG for clone no. 8, 809 bp after the ATG for clone no. 3 and 1176 bp after the ATG for clone no. 29. We chose clone no. 8 for the transformation of *M. grisea*. In fact, in this clone, the transposon was integrated at the beginning of the coding region of the *M. grisea* ILV5 gene (+9 bp after the ATG), resulting in inactivation of the ILV5 gene.

2.3. Transformation of the *M. grisea* Strain P1.2 with the *M. grisea* ILV5 Gene Disrupted in its Coding Region The insert of clone no. 8 containing the *M. grisea* ILV5 gene disrupted in its coding region (9 bp after the ATG) is re-excised from the plasmid by digestion with the ClaI enzyme, and purified on agarose gel. It corresponds to the linearized construct. The plasmid pBC SK+ originating from the undigested clone no. 8 corresponds to the "circular" construct. Transformation of the *M. grisea* strain P1.2. protoplasts is carried out either with 5 μg of the linearized construct or with 4 μg of the "circular" construct. The positive transformation control is performed using 3 μg of plasmid pCB1003 carrying a gene for resistance to hygromycin, and the negative control is carried out without DNA. 62 transformants are obtained for the linearized construct and 24 for the "circular" construct. These 86 transformants were subcultured on complete medium supplemented with hygromycin at 120 g/l and on the minimum medium supplemented with hygromycin at 120 mg/l or at 60 mg/l. This type of subculturing makes it possible to identify the $ilv5^-$ transformants which are auxotrophic for leucine, valine and isoleucine, and which, consequently, do not grow on minimum medium. 8 transformants were thought to be auxotrophic out of the 62 (13%) obtained with the linearized construct, whereas 2 transformants out of 24 (8.3%) were thought to be so with the "circular" construct. The better efficiency in obtaining $ilv5^-$ mutants with the linearized construct compared to the "circular" construct might be explained by the fact that homologous recombination is facilitated with a linearized construct. These transformants are subcultured on "rice flour" medium in order to make them sporulate, the spores are then plated out on complete TNKYE glucose medium and left to germinate in order to effect a single-spore isolation. The single spores are subcultured on TNKYE glucose medium supplemented with hygromycin at 120 mg/l in order to purify the transformants. Identification of the auxotrophic transformants is carried out by subculturing these colonies derived from these single spores on minimum medium, or minimum medium supplemented with leucine, with valine and with isoleucine at 0.3 mM and on complete TNKYE glucose medium. Thus, genetically purified and stable transformants were obtained. Out of 10 potential transformants auxotrophic for leucine, valine and isoleucine, 8 (80%) were found to be effectively auxotrophic. The two nonauxotrophic transformants must have corresponded to a mixture of genetically different populations ($ilv5^+$ and $ilv5^-$) which evolved toward a majority of $ilv5^+$ during growth of the transformant on nonselective medium before single-spore purification.

Example 3

Phenotypic Characterization of the *Magnaporthe grisea* ilv5 Transformants Auxotrophic for Leucine, Valine and Isoleucine and Study of their Pathogenic Potency 3.1. Effect of Disruption of the ILV5 Gene on the Growth and Development of the *M. grisea* Transformants The development of the $ilv5^-$ transformants was tested on various culture media. Thus, on nitrate minimum medium, the $ilv5^-$ transformants are incapable of growing whereas their growth is possible on minimum medium supplemented with valine, leucine and isoleucine at 0.3 mM. The development of the $ilv5^-$ transformants on minimum medium+valine, leucine and isoleucine at 0.3 mM is, however, different than that of the wild-type *M. grisea* strain P1.2. Their growth is in fact slowed down and their mycelium is gray/green, low, flat and sporulating, and not aerial like the wild-type strain. The presence of leucine is not necessary for growth of the $ilv5^-$ transformants, since the results obtained on minimum medium supplemented with isoleucine and valine at 0.3 mM are identical to those obtained on minimum medium supplemented with leucine, valine and isoleucine at 0.3 mM. The development of the $ilv5^-$ transformants or minimum medium supplemented with valine and isoleucine at 0.3 mM can be improved by supplementing the minimum medium with a final concentration of valine and of isoleucine of 1 mM. On complete medium, the $ilv5^-$ transformants exhibit a phenotype which is relatively similar to the wild-type strain: their mycelium is gray/white, and more or less aerial (less aerial than the wild-type strain). The addition of pantotheine, the oxidized form of pantothenate which is involved in leucine biosynthesis, at 1 mg/l to the minimum medium+valine and isoleucine at 0.3 mM does not improve the development of the $ilv5^-$ transformants. The sporulation of the $ilv5^-$ transformants is slower and ten times less on "rice flour" agar medium compared to the wild-type strain. The sporulation of the $ilv5^-$ transformants is almost identical to the wild-type strain when valine and isoleucine are added to the "rice flour" agar medium at a final concentration of 1 mM.

3.2. Tests for the Pathogenic Potency of the $ilv5^-$ Auxotrophic Mutants on Chopped up Barley Leaves under Artificial Survival Conditions The tests for the pathogenic potency of the *M. grisea* $ilv5^-$ transformants were carried out by swabbing or by depositing blocks of test transformant spore suspension onto chopped up barley leaves. One inoculation is carried out using a wet Q-tip soaked in a suspension of spores ($3\times10^4$ spores/ml in general) and used to swab the fragments of barley leaves under artificial survival conditions (on 1% agar-in-water medium, 2 mg/l kinetin). The other type of inoculation consists in depositing drops of 30 μl at three different places on the surface of the barley leaves. The symptoms are observed after incubating for 5 to 9 days at 26° C.

The lesions caused by these mutants are smaller in size than for the wild-type strain and they are 75% fewer in number (see Table 1 below).

TABLE 1

Test for the pathogenic potency of the $ilv5^-$ transformants on barley leaves under artificial survival conditions.

| | Transformants | Average number of lesions per leaf* |
|---|---|---|
| A | L57 ($ilv5^+$) | 4 |
| | L64 ($ilv5^+$) | 4 |
| | L71 ($ilv5^-$) | 1 (−80%) |
| | L85 ($ilv5^-$) | 1 (−80%) |
| B | L41 ($ilv5^+$) | 10 |
| | L21 ($ilv5^-$) | 2 (−80%) |

A. Suspension of spores of the transformants prepared at $3\times10^4$ spores · $ml^{-1}$ B. Suspension of spores of the transformants prepared at $10^5$ spores · $ml^{-1}$

*Number of lesions caused by the M. grisea transformants on barley leaves or in a swab test, 5 days after inoculation (L41 and L21) and 7 days after inoculation (L57, L64, L71, L85).

The lesions caused by the $ilv5^-$ mutants are also atypical and they appear later. They appear after incubation for 6 to 9 days at 26° C., against 4 to 9 days for the wild-type strain (see Table 2 below).

Some lesions caused by the $ilv5^-$ transformants appear at the ends of the barley leaves (Table 2). Injuries at the ends of the leaves might explain these lesions, since they might facilitate penetration of the fungus. Tests for the pathogenic potency of whole plants were consequently carried out in order, firstly, to confirm the existence of a decrease in the pathogenic potency of the ilv5⁻ transformants and, secondly, to estimate the decrease in pathogenesis of the ilv5⁻ mutants and the importance of injuries for penetration of the ilv5⁻ fungus.

TABLE 2

Evolution of the symptoms caused by the *M. grisea* transformants on barley leaves under artificial survival conditions

| Transformants | Drop test 4th day | Drop test 9th day | Swab test 4th day | Swab test 9th day |
|---|---|---|---|---|
| L71 (ilv5⁻) | Absence of lesion | Atypical lesions | Absence of lesion | Absence of lesion (except at the ends of the leaf) |
| L73 (ilv5⁻) | Absence of lesion | Some rare lesions | Absence of lesion | Absence of lesion |
| L85 (ilv5⁻) | One lesion | Atypical lesions | Rare lesions | Rare atypical lesions |
| L63 (ilv5⁻) | Absence of lesion | Atypical lesions | Absence of lesion | Absence of lesion |
| L64 (ilv5⁺) | Sporulating lesions | Gray sporulating lesions | Some sporulating lesions | Gray sporulating lesions |

3.3. Tests for the Pathogenic Potency of the ilv5⁻ Auxotrophic Mutants on Whole Plants The tests for the pathogenic potency of the ilv5⁻ transformants were carried out by spraying a suspension of spores ($10^4$ and $3\times10^4$ spores.ml$^{-1}$) of these transformants onto barley plants. Gelatin at a final concentration of 0.5% (w/v) is added to this spore suspension to enable better adhesion of the spores to the surface of the leaves. The plants are placed in a humid chamber overnight after the inoculation. The symptoms are generally observed after incubation for 5 to 10 days at ambient temperature for barley.

A notable decrease in the symptoms of blast disease on barley is observed in the ilv5⁻ transformants compared to the ilv5⁺ transformant. After incubation for 10 days at ambient temperature, the number of lesions per leaf (approximately 12 cm) varies from 6 to 9 for the ilv5⁻ transformants (L87, L74 and C24) against 37 on average for the ilv5+transformant L57 (see table 3). The number of lesions caused by the ilv5⁻ mutants is therefore reduced by 80% compared to that obtained with the wild-type strain. In addition, the lesions are twice as small for the ilv5⁻ mutants than for the ilv5⁺ transformant (6 mm$^2$ against 13 mm$^2$), and these lesions appear twice as slowly. Specifically, the number of lesions doubled for the ilv5⁻ mutants between the 5$^{th}$ and the 10$^{th}$ day of the experiment, whereas it remained identical for the wild type. The appearance of certain lesions caused by the ilv5⁻ transformants at the ends of the barley leaves under artificial survival conditions suggested that the penetration of the fungus could be facilitated by the injuries inflicted on the barley leaves during the pathogenesis test. However, the results of the pathogenesis tests carried out on the ilv5⁻ transformants on whole plants clearly show a decrease in the pathogenic potency of these mutants of the same order (80%) as on barley leaves under artificial survival conditions.

TABLE 3

Test for the pathogenic potency of the ilv5⁻ transformants on whole plants (barley)

| Transformants | Average number of lesions per barley leaf of 12 cm | Average lesion size (in mm$^2$) |
|---|---|---|
| L57 (ilv5⁺) | 37 ± 9 | 13 |
| L87 (ilv5⁻) | 9 ± 2 (−75%) | 6 (−50%) |
| C24 (ilv5⁻) | 6 ± 2 (−83%) | 4 (−70%) |
| L74 (ilv5⁻) | 8 ± 3 (−80%) | 6 (−50%) |

The inoculation of the barley plants was carried out by spraying a suspension of spores ($3\times10^4$ spores.ml$^{-1}$) of the transformants the pathogenic potency of which it was desired to test. The plants were placed in a humid chamber overnight after the inoculation. The symptoms were observed after incubation for 10 days at ambient temperature. The percentage decreases in the number and the size of the lesions per leaf, calculated with respect to the values obtained for the transformant L57 (ilv5⁺), are indicated in brackets.

Example 4

Fungicidal Effect of the Ketol-acid reductoisomerase Inhibitors 4.1. Fungicidal Effect of the Ketol-acid reductoisomerase Inhibitors on the Phytopathogenic Fungus *Magnaporthe grisea*

The fungicidal effect of the inhibitors dimethylphosphinoyl-2-hydroxyacetate and N-hydroxy-N-isopropyloxamate was tested on the pathogenic fungus *M. grisea* by following the evolution of the growth of this fungus in the presence of various concentrations of inhibitor, over a period of 7 days. Thus, a given culture medium (nitrate minimum medium (MM); MM+leucine, valine and isoleucine at 0.3 mM; complete TNKYE glucose medium (MC); MC+leucine, valine and isoleucine at 0.3 mM) is inoculated with a suspension of spores of the *M. grisea* strain P1.2 at a final concentration of $10^5$ spores/ml. A range of dilutions of the test product, N-hydroxy-N-isopropyloxamate (at pH 5), is prepared in water such that the product is 100 times concentrated. 200 μl of inoculated medium are distributed into a 96-well microplate, to which wells are added 2 μl of 100×-concentrated product. The N-hydroxy-N-isopropyloxamate is tested at final doses of 3; 1; 0.3; 0.1 and 0.03 μM in minimum media and 3 and 0.3 μM in complete media. The microplate is incubated at ambient temperature and reading of the optical density at 630 nm of this microplate makes it possible to follow the growth of the fungus under these various culture conditions at times 0 (beginning of the test) and on days 3, 4, 5, 6 and 7.

This test was carried out by inoculating various culture media with a suspension of spores of the wild-type *M. grisea* strain P1.2. The first experiments were carried out in nitrate minimum medium (MM) and various concentrations of inhibitor were tested. It was the 6$^{th}$ and 7$^{th}$ day of growth before the appearance of significant inhibition of growth in MM medium was observed in the presence of dimethylphosphinoyl-2-hydroxyacetate at 2 mM. The growth is in fact decreased by 50% compared to that of the control without inhibitor. In the presence of the inhibitor N-hydroxy-N-isopropyloxamate (0.3 to 1 μM), from the 3$^{rd}$ day, approximately 50% inhibition of fungal growth is observed in MM medium. The greater inhibition of the *M. grisea* growth by N-hydroxy-N-isopropyloxamate compared to dimethylphosphinoyl-2-hydroxyacetate led us to carry out a more thorough study of this inhibitor.

Figure 2:
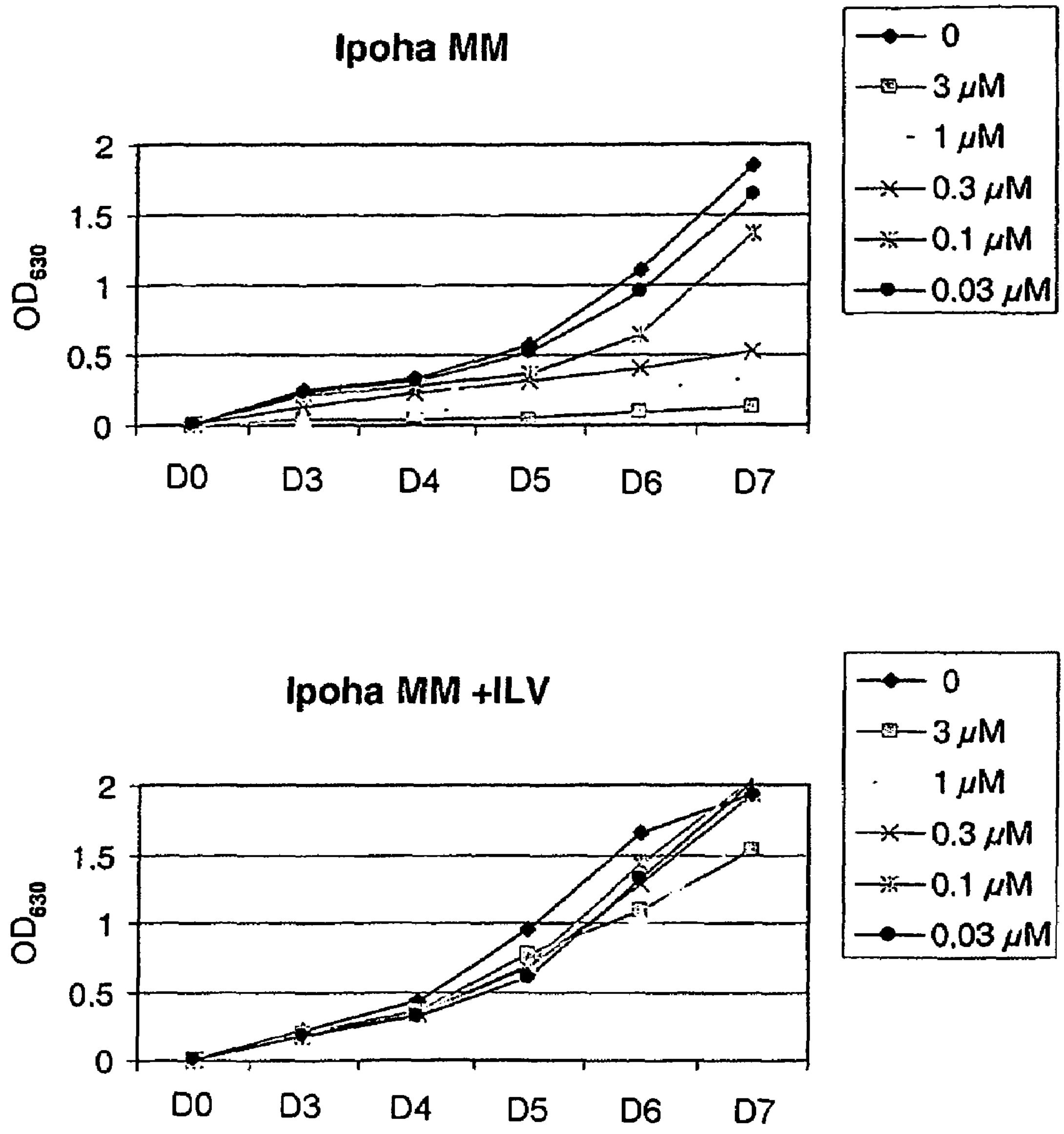
FIG. 2: Growth assay for *M. grisea* in the presence of the inhibitor N-hydroxy-N-isopropyloxamate (IpOHA) and under various culture conditions.

Growth assays for the *M. grisea* fungus were carried out over a period of 7 days, in the presence of the inhibitor N-hydroxy-N-isopropyloxamate (at concentrations ranging from 0.03 μM to 3 μM) in various media (MM and MM supplemented with leucine, valine and isoleucine at 0.3 mM). In minimum medium, N-hydroxy-N-isopropyloxamate strongly inhibits the growth of *M. grisea*. This inhibition of growth by N-hydroxy-N-isopropyloxamate (from 0.3 μM) is observed from the 3rd day of growth, and remains similar on the following days (FIG. 2). We therefore chose to calculate the $ID_{80}$ (concentration of inhibitor such that the inhibition in fungal growth is 80%) and the $ID_{50}$ (concentration of inhibitor such that the inhibition of growth is 50%) on the 5th day of growth. Thus, the growth of the *M. grisea* fungus is decreased by 80% compared to the nontreated control, at an N-hydroxy-N-isopropyloxamate concentration of 1 μM ($ID_{80}$). An N-hydroxy-N-isopropyloxamate concentration of 0.3 μM ($ID_{50}$) inhibits fungal growth by 50% (Table 4).

TABLE 4

Study of the effect of the inhibitor N-hydroxy-N-isopropyloxamate on the growth of the *M. grisea* fungus

| | N-hydroxy-N-isopropyloxamate in μM | | | | | |
|---|---|---|---|---|---|---|
| | 0 (control) | 0.03 | 0.1 | 0.3 | 1 | 3 |
| Minimum medium (MM) | 100 | 92 | 89 | 72 | 56 | 13 |
| MM + ILV | 100 | 77.5 | 83.5 | 81 | 72.5 | 71.5 |

The effect of the inhibitor N-hydroxy-N-isopropyloxamate was tested on the pathogenic fungus *M. grisea* by following the evolution of the growth of this fungus in the presence of various concentrations of inhibitor, in various culture media and over a period of 7 days. The values given in the table correspond to the mean percentages of growth of the *M. grisea* fungus, obtained on the 5th day of growth from two experiments. The control (wild-type strain of *M. grisea*) corresponds to a 100% growth rate. 200 μl of culture medium, minimum medium (MM) or minimum medium+leucine, valine and isoleucine at 0.3 mM (MM+ILV), were inoculated with a suspension of spores of the *M. grisea* strain P1.2 at a final concentration of $10^5$ spores.$ml^{-1}$. The microplate was incubated at ambient temperature and the optical density at 630 nm ($OD_{630}$) was measured on days 0, 3, 4, 5, 6 and 7 (D0, D3, D4, D5, D6 and D7).

The toxicity of the N-hydroxy-N-isopropyloxamate on the growth of the *M. grisea* fungus is lifted by supplementing the minimum medium with valine, leucine and isoleucine at 0.3 mM, whatever the concentration of N-hydroxy-N-isopropyloxamate used. This lifting of N-hydroxy-N-isopropyloxamate toxicity by adding valine, leucine and isoleucine to the minimum medium shows that this toxicity comes from specific inhibition of the biosynthetic pathway for these amino acids, by inhibiting the reductoisomerase.

In fact, the N-hydroxy-N-isopropyloxamate acting specifically on the *M. grisea* reductoisomerase strongly inhibits the growth of *M. grisea* at very low concentrations. The reductoisomerase and the inhibitor N-hydroxy-N-isopropyloxamate proved to be a good target/fungicide couple.

We also sought to determine whether the inhibitor N-hydroxy-N-isopropyloxamate had an effect on germination of the *M. grisea* spores. A microscopic observation of the *M. grisea* spores during the experiments carried out previously in minimum medium, in the presence of N-hydroxy-N-isopropyloxamate at 1 and 3 μM on days 0 and 2 showed that spore germination was not blocked. Additional tests were carried out in order to determine whether, at high concentrations, N-hydroxy-N-isopropyloxamate could block spore germination. Thus at 10 mM, N-hydroxy-N-isopropyloxamate does not inhibit *M. grisea* spore germination either in water or in minimum medium, at 24 and at 72 hours. The inhibition of *M. grisea* growth by N-hydroxy-N-isopropyloxamate only manifests itself after germination, during growth of the hyphae. It may therefore be supposed that use of the amino acid (valine and isoleucine) stores present in the spore could, initially, allow germination. Limitation of the amino acid stores and more or less rapid exhaustion thereof could act as a factor limiting *M. grisea* growth.

4.2 Fungicidal Effect of the Ketol-acid reductoisomerase Inhibitors on Other Fungi The toxicity of IpOHA with respect to other fungal species such as *Pythium ultimum, Botrytis cinerea, Ustilago nuda* and *Mycosphaerella graminicola* was measured under the same conditions as for *M. grisea* (culture in liquid minimum medium in 96-well microplates). The growth of *Botrytis cinerea* is not affected by the highest concentration of IpOHA used (30 μM), which shows that this species is resistant to IpOHA. The growth of *Ustilago nuda* and of *Pythium ultimum* is inhibited by IpOHA starting from 10 μM. The growth of *Mycosphaerella graminicola* is inhibited from 0.3 μM (Table 5). When the minimum medium (MM-liq) is supplemented with isoleucine, leucine and valine (1 mM), the IpOHA toxicity is lifted for all the sensitive fungal species. On the other hand, with a concentration of 0.3 mM, the inhibition is lifted in *Ustilago nuda* only for IpOHA concentrations of less than 30 μM. IpOHA has a strong action on the growth of *Mycosphaerella graminicola*.

TABLE 5

Toxicity of IpOHA for various fungal species

| | $ID_{80}$ | $ID_{50}$ | Level of sensitivity to IpOHA |
|---|---|---|---|
| *Botrytis cinerea* | / | / | Resistant |
| *Pythium ultimum* | 30 | 10 | Moderately sensitive |
| *Ustilago nuda* | 30 | 3 | Moderately sensitive |
| *Mycosphaerella graminicola* | 3 | 1 | Sensitive |
| *Magnaporthe grisea* | 3 | 1 | Sensitive |

$ID_{50}$: concentration which inhibits fungal growth by 50%.
$ID_{80}$: concentration which inhibits fungal growth by 80%.

Example 5

Biochemical Studies of the Ketol-acid reductoisomerase of *S. cerevisiae*

The coding sequence of the yeast ILV5 gene without the transit peptide was overexpressed in *E. coli* in order to obtain large amounts of enzyme so as to facilitate the biochemical study thereof and in particular the structural study thereof.

The strategy employed for studying the yeast reductoisomerase was as follows: the yeast reductoisomerase ILV5 gene was initially amplified by PCR without the portion encoding the transit peptide. The PCR reaction product was then cloned into an IPTG-inducible expression vector pET. The reductoisomerase was then overproduced in *E. coli* and purified, and then its biochemical properties were studied.

5.1 PCR Amplification and Cloning of the Portion of the Yeast Reductoisomerase ILV5 Gene Encoding the Mature Protein The signal peptide, which allows adjusting of the yeast reductoisomerase into its cellular compartment, the mitochondrium, is cleaved when the protein has penetrated into the mitochondrium. We therefore chose to clone the ILV5 gene without the region encoding the transit peptide in order to overproduce the yeast reductoisomerase corresponding to the mature protein in *E. coli.*

The region of the yeast ILV5 gene located between the end of the transit peptide and the translation-terminating STOP codon was amplified by PCR from the genomic DNA of *S. cerevisiae* with the pairs of primers (1'-3') and (2'-3'). The size of the DNA fragments amplified with the pairs of primers (1'-3') and (2'-3') is 1079 bp and 1124 bp, respectively. These DNA fragments were purified after separation by electrophoresis, and then digested and cloned into the vector PET-23d at SalI/NcoL A double digestion of the cloning vector and of the PCR reaction product with the NcoI and SalI enzymes in fact enables the yeast ILV5 gene to be cloned into the vector PET-23d, in the correct orientation. The plasmid pET-23d (Tebu), carrying the gene for resistance to ampicillin, is used as an inducible expression vector to produce a large amount of the yeast reductoisomerase in *E. coli*. This type of vector has a T7 phage promoter, which is recognized by the T7 RNA polymerase but not by the RNA polymerase of *E. coli*. Production of the cloned protein takes place after IPTG induction of the strain BL21 pLysS (resistant to chloramphenicol); in this bacterial strain, the T7 RNA polymerase gene is under the control of the IPTG-inducible lac promoter. The strain BL21 pLysS transformed with the plasmid pET-23d, carrying the *S. cerevisiae* ILV5 gene, is called BL21 pLysS-pET-23d-reductoisomerase. Construct no. 1 corresponds to the cloning of the fragment amplified with the primers (1'-3') and construct no. 2 corresponds to the cloning of the DNA fragment amplified with the primers (2'-3'). A SalI/NcoI double digestion of the 12 clones obtained after transformation of the DH5 cells with construct no. 1 and of the 6 clones transformed with construct no. 2 makes it possible to re-excise the fragment cloned into the vector pET and to thus verify the presence of one of the two constructs in the various clones. Analysis of the digestion profiles for these bacterial clones showed that they all possess the corresponding construct.

Two clones were selected: clone PET 1–4 (construct no. 1) and clone PET 2-1 (construct no. 2); they were used to transform BL21 pLysS cells in order to overproduce the yeast reductoisomerase in *E. coli.*

5.2 Purification of the Yeast Reductoisomerase Overproduced in *E. coli*

Overexpression of the "short" form (construct no. 1) and of the "long" form (construct no. 2) of the yeast reductoisomerase was induced in *E. coli* with IPTG. The bacterial strain BL21 pLysS, transformed with the plasmid pET 23-d containing the yeast ILV5 gene without the region encoding the transit peptide, is cultured at 28° C. with shaking in LB medium supplemented with carbenicillin (100 mg/l) and with chioramphenicol (30 mg/l) until a density equivalent to an $OD_{600}$ of approximately 0.6 is obtained. The IPTG is then added at a final concentration of 0.4 mM and the bacteria are left in culture at 28° C. with shaking for approximately 15 hours. This bacterial culture is then centrifuged (30 minutes, 4500 rpm); the bacterial pellet is resuspended in 15 ml of buffer (10 mM $KH_2$—$K_2PO_4$ (pH 7.5), 1 mM EDTA, 1 mM DTT and protease inhibitors: 1 mM benzamidine HCl, 5 mM aminocaproic acid) and sonicated using a VIBRA-CELL™ disruptor (Sonics and Materials, Danbury, Conn., U.S.A) for 15 minutes, at power 4, 40% of the total lysis time. The cell extract is centrifuged (20 minutes, 15 000 rpm); the supernatant, containing the soluble proteins, is then conserved at −80° C.

Analysis of the total protein fractions and of the soluble protein fractions on acrylamide gel showed that the "short" and "long" forms of the yeast reductoisomerase are present in the soluble protein fraction and that they represent approximately 25 to 30% of these proteins. Since the most probable position for the yeast reductoisomerase transit peptide cleavage site is located between amino acids 47 and 48 of the protein sequence of this enzyme (Petersen, G. L. et al., *NAR* 14, 24:9631–9650, 1986), we chose to continue working with the short form of the yeast reductoisomerase.

Purification of the short form of the reductoisomerase was therefore carried out in two steps using the soluble protein fraction; first, on an anion exchange column (Q-SEPHAROSE™), and then on a permeation column (SUPERDEX 75™). The soluble protein extract (15.5 ml; 227.8 mg of proteins), which contains the yeast reductoisomerase (crude extract), is applied to an anion exchange column, HiLoad 16/10 Q-SEPHAROSE™ (Pharmacia), connected to a Pharmacia FPLC™ system, pre-equilibrated with 10 mM $KH_2$—$K_2PO_4$ buffer/1 mM EDTA/1 mM DTT. The enzyme is eluted with 78 ml of this same buffer (flow rate=1 ml/mm; fraction size3 ml). The chromatographic fractions containing the yeast reductoisomerase are concentrated to 1.6 ml by centrifugation at 5500 rpm in a macrosep-10 unit (filtron). This extract (27.7 mg) is then applied to a HiLoad 16/60 Superdex 75 column (Pharmacia) connected to a Pharmacia FPLC™ system, pre-equilibrated with 25 mM Hepes-KOH buffer. The enzyme is eluted with 58 ml of this same buffer (flow rate=1 ml/min; fraction size=1 ml). The chromatographic fractions containing the yeast reductoisomerase (18.99 mg) are concentrated to 9.7 mg/ml by centrifugation at 5500 rpm in a 10K MICROSEP™ (filtron) and conserved at −80° C.

After injection of the soluble protein fraction (approximately 230 mg) onto the Q-SEPHAROSE™ column, the yeast reductoisomerase is diluted with 10 mM $KH_2$—$K_2PO_4$ buffer/1 mM EDTA/1 mM DTT. There is in fact no need to elute this enzyme through the action of an increasing concentration gradient of phosphate buffer since preliminary experiments have shown that this enzyme is not retained by the column. After this first purification step, approximately 30 mg of protein were recovered and the yield from the purification in terms of activity is 55% (Table 6).

TABLE 6

| Purification steps | Steps for purifying the yeast reductoisomerase overexpressed in *E. coli* | | | | | |
|---|---|---|---|---|---|---|
| | Amount of proteins (mg) | | Total activity (μmol of NADPH oxidized. | Specific activity (total activity/$mg^{-1}$ of proteins) | | |
| | Bradford | 205 | $min^{-1}$) | Bradford | 205 | Yield in % |
| Crude extract of soluble proteins | 227.82 | n.d. | 134.16 | 0.59 | n.d. | 100 |
| Q-Sepharose fraction pool | 27.72 | 14.34 | 73.22 | 2.64 | 5.11 | 54.58 |
| Superdex 75 fraction pool | 18.99 | 8.4 | 45.85 | 2.4 | 5.46 | 34.18 |

The activities were determined in the following reaction medium: 50 mM sodium Hepes, pH 7.5; 10 mM $MgCl_2$; 250 μM NADPH and 0.48 mM AHB.
The proteins were assayed according to the Bradford method (Bradford) or by measuring the absorbence at 205 nm (205).
n.d. = not determined.

Analysis of the Q-SEPHAROSE™ fraction pool on acrylamide gel shows that, after this first purification step, the enzyme is virtually pure. The Q-SEPHAROSE™ fraction pool is injected onto the gel filtration column and the yeast reductoisomerase is eluted with 25 mM Hepes-KOH buffer. After this $2^{nd}$ purification step, approximately 20 mg of pure protein are recovered; the final yield from the two steps for purifying the yeast reductoisomerase is approximately 34%.

5.3 Studies of the Kinetic Properties of the Yeast Reductoisomerase Overproduced in *E. coli*

The kinetic parameters for the yeast reductoisomerase were determined by following the evolution of the enzyme reaction in the spectrophotometer under saturating conditions with respect to magnesium, to NADPH and to AHB or AL substrate. All the enzyme activity measurements were carried out in a quartz cuvette with an optical path of 1 cm, containing sodium Hepes buffer (50 mM, pH 7.5), 10 mM $MgCl_2$, 250 μM NADPH, in a final volume of 1 ml, at 25° C. The enzyme reaction was initiated by adding 0.48 mM of AHB or of AL. The evolution of this reaction was followed by virtue of the decrease in absorption of NADPH at 340 nm.

5.3.1. Determination of the Optimum pH for Activity of the Purified Recombinant Yeast Reductoisomerase In order to determine the optimum conditions for carrying out the kinetic measurements on the yeast reductoisomerase, the optimum pH for activity of this enzyme was determined, by measuring the activity of the purified enzyme in buffers of varying pH. The optimum pH for activity of the yeast reductoisomerase is 7.5, although studies had shown that that of plant reductoisomerase is 8.2. This difference in optimum pH for reductoisomerase activity between plants and yeast is explained by the cellular location of these two enzymes. The plant reductoisomerase is located in the chloroplast, the pH of which is 8.2 in light, whereas the yeast reductoisomerase is located in the mitochondrium, the pH of which is 7.5. The optimum pH for activity of the reductoisomerase is therefore well suited to the cellular environment in which they are found.

5.3.2. Determination of the Kinetic Parameters for the Purified Recombinant Yeast Reductoisomerase The affinity of the yeast reductoisomerase for its various ligands was studied.

(a) Specific Activities

The specific activities of the yeast reductoisomerase for the AHB and AL substrates are 6 and 1 μmol of NADPH oxidized.$min^{-1}$.$mg^{-1}$ of protein, respectively. The ratio of the maximum rate ($V_m$) of enzyme reaction in the presence of the AHB substrate to the maximum rate ($V_m$) of enzyme reaction in the presence of the acetolactate substrate is therefore unchanged for the yeast enzyme compared to the plant enzyme ($V_m$AHB/$V_m$AL=6). The specific activities of the plant reductoisomerase for the AHB and AL substrates are, moreover, 6 and 1 μmol of NADPH oxidized.$min^{-1}$.$mg^{-1}$ of protein, respectively.

(b) Affinities for the Cofactors NADPH and NADH

The affinity of the yeast reductoisomerase for NADPH is very high (FIG. 3). In fact, a Km for this cofactor of 1.6 μM was measured. This $K_M$ is relatively similar to that measured for the plant enzyme ($K_M$=5 μM). The $K_M$ NADPH value obtained for the purified yeast reductoisomerase is coherent with the value obtained for the partially purified yeast enzyme ($K_M$<2.5 μM; Hawkes et al., 1989). However, unlike the plant enzyme, which is capable of using NADH, with a very low affinity ($K_M$ NADH=645 μM in the presence of AHB and of $Mg^{2+}$; Dumas et al., *Biochem. J.*, 288:865–874, 1992), the yeast enzyme appears to be incapable of using NADH. No enzyme activity was detected in the presence of NADH (at 300 μM) under saturating conditions with respect to AHB substrate and to magnesium, perhaps due to the affinity for NADH being even lower than that of the plant reductoisomerase. The yeast reductoisomerase is thought to use NADPH as a hydrogen donor with a specificity which is even more marked than the plant enzyme.

(c) Affinities for the AHB and AL Substrates

The affinity of the yeast reductoisomerase for the AHB substrate ($K_M$=104 μM for the racemic form) is approximately 5 times lower than that of the plant reductoisomerase; whereas the affinity of the yeast reductoisomerase for the AL substrate ($K_M$=266 μM for the racemic form) is 10 times lower than the plant reductoisomerase (FIG. 4). These $K_M$ values are quite close to those obtained for the partially purified enzyme of *N. crassa*. Specifically, the $K_M$ AHB and AL values for the *N. crassa* reductoisomerase are 160 μM and 320 μM, respectively.

The most noteworthy difference in biochemical properties between the yeast reductoisomerase and plant reductoisomerase is the affinity of this enzyme for magnesium.

(d) Affinities for Magnesium

The affinity of the yeast reductoisomerase ($K_M$=968 μM) is in effect 200 times lower than that of the plant enzyme ($K_M$=approximately 5 μM). See FIG. 5. This low affinity of the yeast reductoisomerase for magnesium could be a characteristic of the fungal reductoisomerase. In fact, studies carried out on the *N. crassa* reductoisomerase have shown that this enzyme has a $K_M$ magnesium of 580 μM in the presence of NADPH and of the AHB substrate (Kritani et al., J. Biological Chemistry, 241:2047–2051, 1965). Comparison of the primary sequences of the yeast, *N. crassa* and plant reductoisomerases showed that the main difference between these three enzymes was the absence within the fungal protein of a 140 amino acid sequence involved in the interaction between the two monomers of the plant enzyme. The two domains known to bind $Mg^{2+}$ ions in the plant enzyme are, however, present in the yeast enzyme. The study of a monomeric mutant of the plant reductoisomerase obtained by deleting 7 amino acids in the 140 amino acid dimerization region showed that the enzyme exhibits a much lower affinity for magnesium ($K_M$=640 μM) than the wild-type form of the enzyme (Wessel et al., *Biochemistry,* 37:12753–12760, 1998). The quaternary structure of the plant reductoisomerase is therefore thought to play a role in stabilizing the active site of the plant enzyme and the high affinity sites for magnesium. Thus, although the yeast reductoisomerase clearly possesses the two $Mg^{2+}$ ion-binding domains, the absence of the sequence of this 140 amino acid region within the yeast enzyme could explain the lower affinity of the yeast reductoisomerase for magnesium by virtue of the spatial organization of the active site of this enzyme, which is probably different from that of the plant enzyme. Although the magnesium-binding sites of the yeast reductoisomerase have a much lower affinity for this cation, the affinity of the yeast enzyme for NADPH is similar to that of the plant enzyme. It may therefore be supposed that the conformation of the yeast reductoisomerase could be such that the amino-terminal domain which is involved in the binding of NADPH is relatively similar to that of the plant enzyme and that the carboxy-terminal domain which is responsible for the binding of the two magnesium atoms and of the substrate is different than that of the plant enzyme. A knowledge of the quaternary structure of the yeast reductoisomerase through crystallization of the enzyme would make it possible to explain this low affinity for $Mg^{2+}$ ions.

5.4 Study of the Effect of the Inhibitors N-hydroxy-N-isopropyloxamate and Dimethylphosphinoyl-2-Hydroxyacetate on the Yeast Reductoisomerase 5.4.1 Study of the Stoichiometry of Binding of the Inhibitors N-hydroxy-N-Isopropyloxamate and Dimethylphosphinoyl-2-Hydroxyacetate to the Yeast Reductoisomerase The study of the stoichiometry of binding of the inhibitors N-hydroxy-N-isopropyl-oxamate and dimethylphosphinoyl-2-hydroxyacetate was carried out by incubating varying amounts of enzyme (from 0.1 to 0.4 nmol) with a constant amount of inhibitor for 20 minutes, with 25 nmol of NADPH and 0.25 μmol of $MgCl_2$, in a final volume of 10 μl. The reactions are initiated by adding 0.48 mM AHB in 50 mM sodium Hepes buffer, pH 7.5, containing 10 mM $MgCl_2$.

Figure 6:
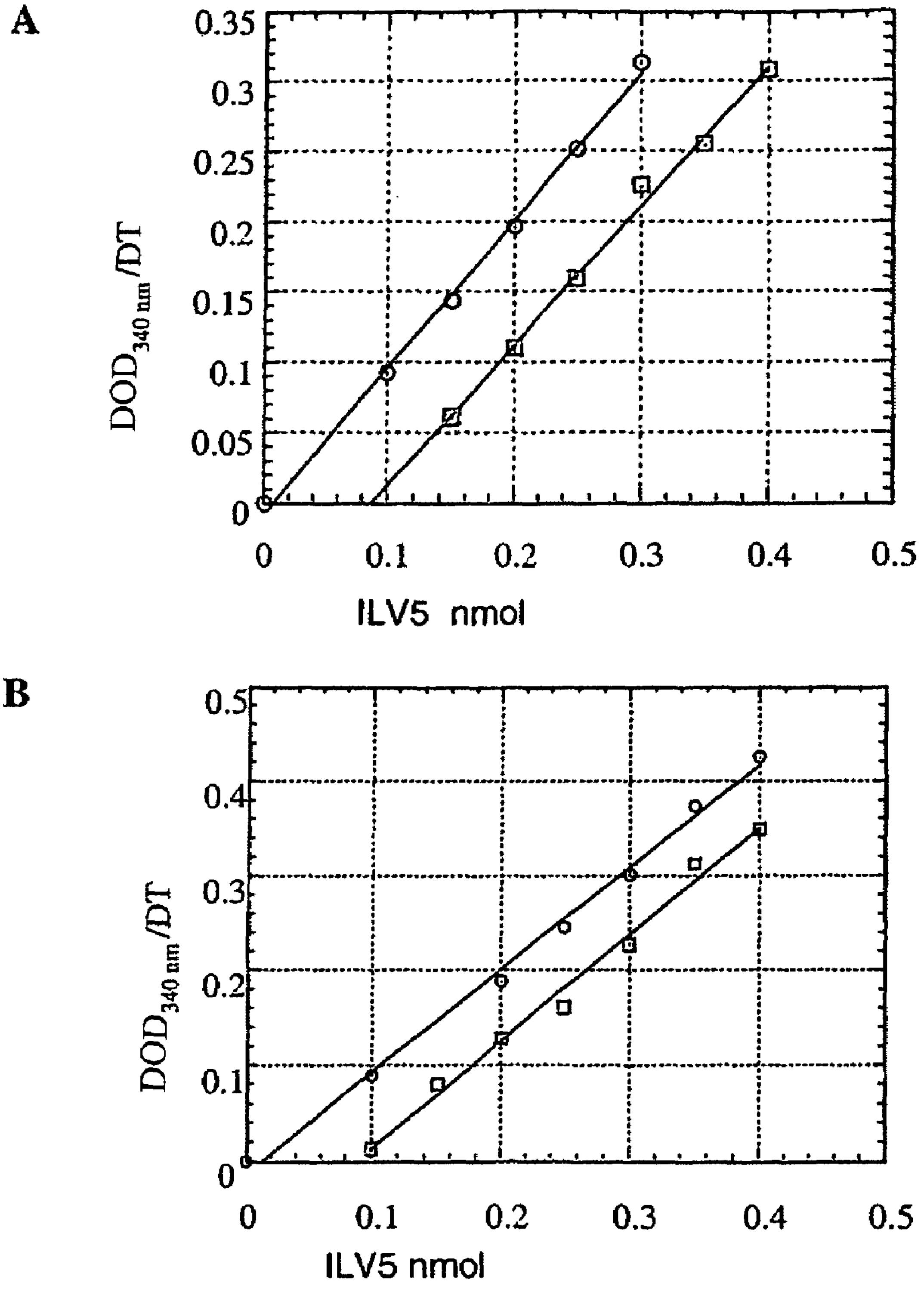

In the presence of 0.1 nmol of dimethylphosphinoyl-2-hydroxyacetate, an enzyme activity is detected only with amounts of enzyme greater than 0.09 mmol. Similarly, in the presence of 0.1 nmol of N-hydroxy-N-isopropyloxamate, an enzyme activity is detected only for amounts of enzyme greater than 0.1 nmol (FIG. 6). In addition, for these two inhibitors, when the enzyme is in excess relative to the inhibitor in the reaction medium, the enzyme activities increase in parallel with those of the control without inhibitor. N-hydroxy-N-isopropyloxamate and dimethylphosphinoyl-2-hydroxyacetate are therefore thought to act on the yeast reductoisomerase as irreversible inhibitors. In fact, in the case of irreversible inhibition, in the presence of a low amount of enzyme, all the enzyme complexes with the inhibitor. The enzyme activity is then zero, since there is no longer any free enzyme in the reaction medium. When the amount of enzyme present in the reaction medium is greater than the amount of inhibitor, the free enzyme in excess in the medium then behaves like the control without inhibitor (straight line parallel to the control). Moreover, since 0.1 nmol of inhibitor (N-hydroxy-N-isopropyloxamate or dimethylphosphinoyl-2-hydroxyacetate) is necessary to completely inhibit 0.1 nmol of enzyme, the stoichiometry of binding of the inhibitors to the yeast reductoisomerase is, consequently, 1 mol of inhibitor per mole of enzyme.

5.4.2 Study of the Rate of Binding of the Inhibitors N-hydroxy-N-isopropyloxamate and Dimethylphosphinoyl-2-Hydroxyacetate to the Yeast Reductoisomerase The effect of the inhibitors N-hydroxy-N-isopropyloxamate and dimethylphosphinoyl-2-hydroxyacetate on the yeast reductoisomerase was followed over time by measuring the decrease in absorbence of NADPH at 340 nm, in a spectrophotometer. Each measurement is carried out under saturating conditions with respect to $MgCl_2$ (10 mM) and with respect to NADPH (0.25 mM) for a period of 6 minutes in the presence of a given concentration of inhibitor (N-hydroxy-N-isopropyloxamate=15 μM or dimethylphosphinoyl-2-hydroxyacetate=10 μM) and of enzyme (110 nM); the concentration of AHB substrate used ranges from 250 μM to 2375 pM. The study of the stoichiometry of binding of the inhibitors N-hydroxy-N-isopropyloxamate and dimethylphosphinoyl-2-hydroxyacetate to the yeast reductoisomerase showed that these inhibitors behave like irreversible inhibitors. Equation (1) therefore makes it possible to describe the kinetics of formation of the reaction product, this equation being applicable to irreversible inhibitors. The parameters m1, m2 and m3, defined on the basis of equation (1), are obtained directly from the adjustment of the experimental curves using the KaleidaGraph program, along with the errors associated with the determination of these parameters.

Equation (1):

$$OD_{340}=m_1+(m_2-m_1).e^{(-m3.t)}$$

where the parameters are as follows:

- $OD_{340}$ is the optical density measured on a spectrophotometer at 340 nm at time "t"
- $m_1$ the optical density when "t" tends toward infinity
- $m_2$ the initial optical density
- $m_3$ the product of the concentration of inhibitor multiplied by the apparent disappearance constant for NADPH.

Figure 9:
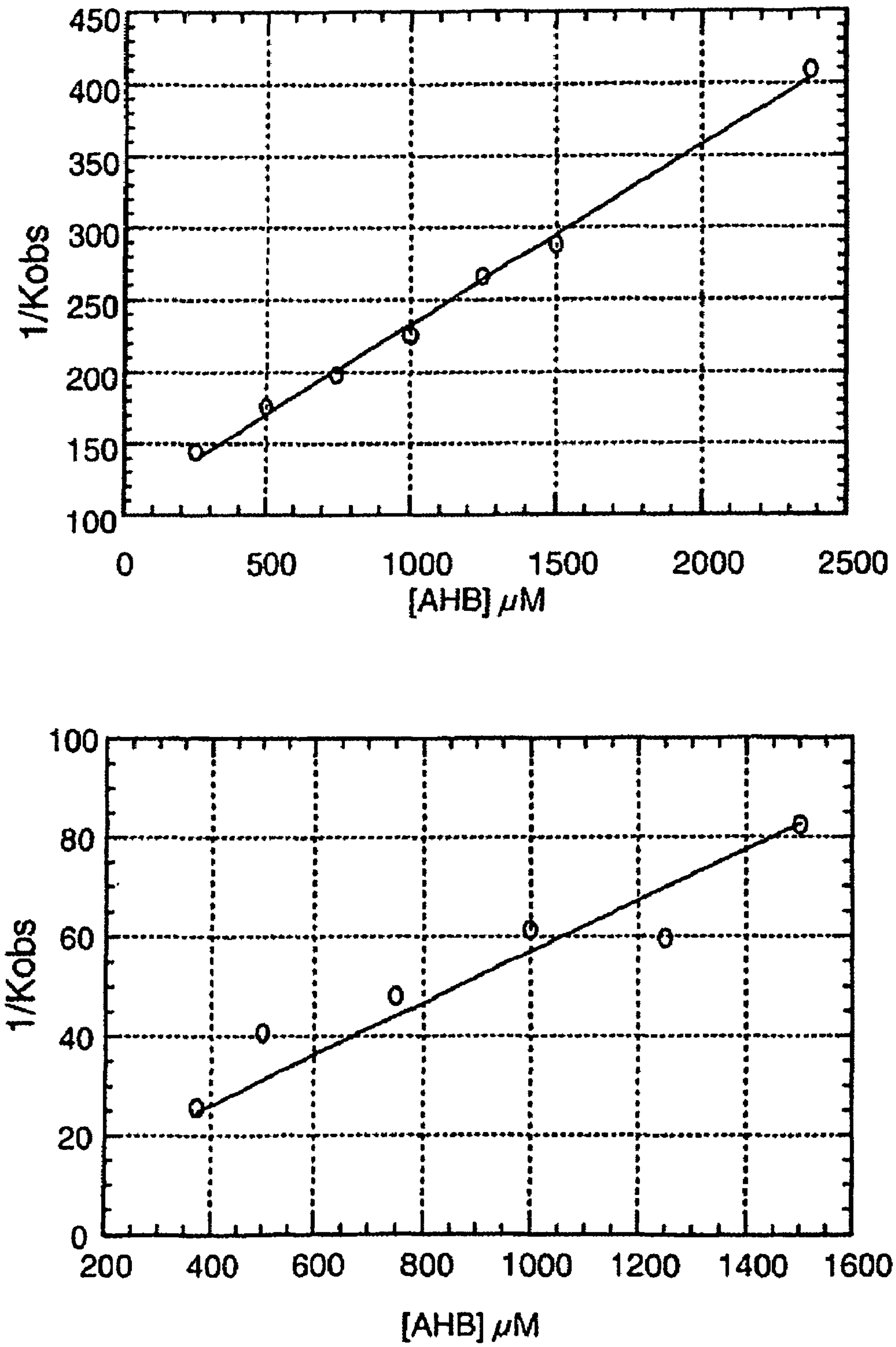

For a reversible inhibition, two cases may occur: either the inhibitor binds directly to the enzyme in a single step, or it binds to the enzyme in two steps, forming a reversible enzyme/inhibitor intermediate complex. The graphic representation $m_3$ as a function of the concentration inhibitor makes it possible to define the type of irreversible inhibition. Thus, to determine whether the inhibitors N-hydroxy-N-isopropyloxamate and dimethylphosphinoyl-2-hydroxyacetate bind to the yeast reductoisomerase in one or two steps, the effect of these inhibitors on the enzyme activity of this enzyme is followed over time (6 min) by varying the concentration of inhibitor, for given concentrations of enzyme (110 nM) and AHB (0.48 mM) (FIG. 7). For a simple irreversible inhibition, without formation of the reversible enzyme/inhibitor intermediate complex, the apparent rate of formation of the enzyme/inhibitor complex ($K_{obs}$ or $m_3$) is a linear function of the concentration of inhibitor. If the irreversible inhibition involves the existence of a reversible intermediate complex, the graphic representation $m_3$ as a function of the concentration of inhibitor is a hyperbola. For the inhibitors N-hydroxy-N-isopropyloxamate and dimethylphosphinoyl-2-hydroxyacetate, the graphic representation $m_3$ as a function of the concentration of inhibitor is linear, suggesting that the inhibition of the yeast reductoisomerase by these products occurs in a single step (FIG. 8), as is the case for inhibition of the plant reductoisomerase. However, even taking into account experimental errors, the graphic representations $m_3$ as a function of the concentration of inhibitor do not pass through the origin for the two inhibitors. These two inhibitors, N-hydroxy-N-isopropyloxamate and dimethylphosphinoyl-2-hydroxyacetate, might not be entirely irreversible. In this case, the dissociation constant for the enzyme/inhibitor complex, $k_{-0}$, could have a non-negligible value. The mechanism of inhibition (competitive or noncompetitive) can be determined by studying the effect of the concentration of substrate on the apparent rate of formation of the enzyme/inhibitor complex. This determination is carried out using the graphic representation $1/m_3$ as a function of the concentration of substrate. For competitive inhibitors, the graphic representation $1/m_3$ as a function of the concentration of substrate is linear. For noncompetitive inhibitors, the parameter $m_3$ is independent of the concentration of substrate. For the inhibitors N-hydroxy-N-isopropyloxamate and dimethylphosphinoyl-2-hydroxyacetate, the inverse of $m_3$ varies in a linear fashion as a function of the concentration of AHB substrate. N-hydroxy-N-isopropyloxamate and dimethylphosphinoyl-2-hydroxyacetate therefore behave like inhibitors of the yeast reductoisomerase which are competitive with respect to the AHB substrate (FIG. 9). The inhibitor/yeast enzyme association constant ($k_0$) is then calculated by virtue of equation (2).

Equation (2):

$$k_{obs} = \frac{k_0 \cdot [I]}{1 + \frac{[S]}{K_M^S}} + k - 0$$

$k_{obs}$=$m_3$=apparent rate of formation of the enzyme/inhibitor complex $k_0$=inhibitor/enzyme association constant $k_{-0}$=inhibitor/enzyme dissociation constant $K^S_M$=Michaelis-Menten constant for the AHB substrate

[I]=concentration of inhibitor

[S]=concentration of substrate

For irreversible inhibitors, the $k_{-0}$ can be considered to be negligible, the $k_0$ is then calculated by virtue of equation (3) using the KALEIDAGRAPH™ program.

Equation (3):

$$\frac{1}{m_3} = \frac{1}{k_0 \cdot [I]} + \frac{1}{K_M^S \cdot [I] \cdot k_0} \cdot [S]$$

This equation can be used for the inhibitor N-hydroxy-N-isopropyloxamate, but not for dimethylphosphinoyl-2-hydroxyacetate. For dimethylphosphinoyl-2-hydroxyacetate, the graphic representation $1/m_3$ as a function of the concentration of substrate is linear, but does not pass through the origin. For N-hydroxy-N-isopropyloxamate, a graphic representation $1/m_3$ as a function of the concentration of substrate is linear and the value on the y-axis at the origin is negligible. A hypothesis which may explain this result is: the inhibitor dimethylphosphinoyl-2-hydroxyacetate is perhaps not completely irreversible. A linear regression line then makes it possible to obtain the value of the $k_0$ for dimethylphosphinoyl-2-hydroxyacetate. The values of $k_0$ corresponding to the inhibitors N-hydroxy-N-isopropyloxamate and dimethylphosphinoyl-2-hydroxyacetate are 12 433 $M^{-1}.s^{-1}$ and 7721 $M^{-1}.s^{-1}$, respectively. Thus, unlike the plant reductoisomerase ($k_0$ for N-hydroxy-N-isopropyloxamate=1900 $M^{-1}.s^{-1}$ and $k_0$ for dimethylphosphinoyl-2-hydroxyacetate=22 000 $M^{-1}.s^{-1}$), N-hydroxy-N-isopropyloxamate is a better inhibitor of the yeast enzyme than dimethylphosphinoyl-2-hydroxyacetate.

5.5. Structural Study of the Yeast Reductoisomerase

The quaternary structure of the yeast reductoisomerase was studied according to two different approaches: mass spectrometry and gel filtration.

The existence of two different states of oligomerization was demonstrated by means of mass spectrometry under nondenaturing conditions. This technique showed that the yeast reductoisomerase is present mainly in dimeric form, but a minor monomeric form is also present. The dimer is represented by a charge state distribution $[D+18H]^{18+}$ to $[D+21H]^{21+}$. A small presence of monomer of the yeast reductoisomerase, represented by the charge states $[M+12H]^{12+}$ to $[M+14H]^{14+}$, is demonstrated on this same mass spectrum. The yeast reductoisomerase could therefore be in equilibrium between a monomeric form and a dimeric form.

Application, to gel filtration (SUPERDEX 75™), of the pool of yeast reductoisomerase fractions obtained after the $1^{st}$ purification step shows that the reductoisomerase is eluted in a single peak and that its molecular mass is estimated at 67 kDa. Now, the expected molecular mass of the monomeric form of this enzyme is approximately 40 kDa and 80 kDa for the dimeric form under nondenaturing conditions. The molecular mass which is intermediate between the monomeric and dimeric forms of the yeast reductoisomerase confirms the existence of an equilibrium between these two forms of the enzyme. Only a rapid dynamic equilibrium between these two forms could explain a single elution peak being obtained in gel filtration. Specifically, if this equilibrium was slow, two elution peaks would have been observed on exiting gel filtration; one would correspond to the monomeric form, and the other to the dimeric form of the enzyme.

DOCUMENTS CITED

All sequences, patents, patent applications or other published documents cited anywhere in this specification are herein incorporated in their entirety by reference to the same extent as if each individual sequence, publication, patent, patent application or other published document was specifically and individually indicated to be incorporated by reference.

We claim:

1. A method for identifying a fungicidal compound, comprising:

a) contacting a ketol-acid reductoisomerase with a test compound under conditions required for ketol-acid reductoisomerase enzymatic activity and in the presence of a substrate, wherein the ketol-acid reductoisomerase comprises an amino acid sequence selected from the group consisting of SEQ ID NO:1, SEQ ID NO:2, and SEQ ID NO:3 and b) measuring the ketol-acid reductoisomerase enzymatic activity;

wherein inhibition of ketol-acid reductoisomerase activity by the test compound indicates that the test compound is a fungicidal compound.

2. The method of claim 1, further comprising determining whether said compound that inhibits the enzymatic activity of a ketol-acid reductoisomerase inhibits fungal growth and pathogenesis.

3. The method of claim 1, wherein the ketol-acid reductoisomerase is contacted with the test compound in the presence of magnesium and NADPH.

4. The method of claim 1, wherein said substrate is 2-acetolactate (AL) or 2-aceto-2-hydroxybutyrate (AHB).

5. The method of claim 1, wherein said measuring the ketol-acid reductoisomerase enzymatic activity comprises measuring the decrease in absorption of NADPH at 340 nm.

6. A method for identifying a fungicidal compound comprising:

a) expressing in a host organism a ketol-acid reductoisomerase comprising an amino acid sequence selected from the group consisting of SEQ ID NO: 1, SEQ ID NO:2, and SEQ ID NO:3;

b) purifying the ketol-acid reductoisomerase produced by said host organism;

c) under conditions required for ketol-acid reductoisomerase enzymatic activity and in the presence of a substrate, contacting a test compound with said purified ketol-acid reductoisomerase; and d) measuring the ketol-acid reductoisomerase enzymatic activity, wherein inhibition of ketol-acid reductoisomerase activity by the test compound indicates that the test compound is a fungicidal compound.

7. The method of claim 6, wherein said substrate is 2-acetolactate (AL) or 2-aceto-2-hydroxybutyrate (AHB).

8. The method of claim 6, wherein said measuring the ketol-acid reductoisomerase enzymatic activity comprises measuring a decrease in absorption of NADPH at 340 nm.

* * * * *